US006633785B1

(12) United States Patent
Kasahara et al.

(10) Patent No.: US 6,633,785 B1
(45) Date of Patent: Oct. 14, 2003

(54) THERMAL CYCLER AND DNA AMPLIFIER METHOD

(75) Inventors: Akihiro Kasahara, Chiba-ken (JP); Koichiro Kawano, Kanagawa-ken (JP); Hideo Iwasaki, Kanagawa-ken (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 519 days.

(21) Appl. No.: 09/651,085

(22) Filed: Aug. 30, 2000

(30) Foreign Application Priority Data

Aug. 31, 1999 (JP) ........................................ P11-246307

(51) Int. Cl.[7] ............................ G05B 21/02; C12Q 1/68

(52) U.S. Cl. ........................... 700/73; 700/90; 700/300; 702/20; 435/286.1; 435/287.2

(58) Field of Search .............................. 700/73, 74, 90, 700/299, 300; 435/3, 285.1, 286.1, 287.1, 287.2; 702/19, 20, 130

(56) References Cited

U.S. PATENT DOCUMENTS 4,683,202 A 7/1987 Mullis ....................... 435/91.2
5,123,477 A * 6/1992 Tyler ............................. 165/2
5,187,084 A * 2/1993 Hallsby ....................... 435/91
5,281,516 A * 1/1994 Stapleton et al. .............. 435/3
5,475,610 A 12/1995 Atwood et al. ............. 700/269
5,985,651 A * 11/1999 Hunicke-Smith ........ 435/285.1
6,074,868 A * 6/2000 Blumenfeld ............. 435/286.1

* cited by examiner

*Primary Examiner*—Paul P. Gordon
(74) *Attorney, Agent, or Firm*—Oblon, Spivak, McClelland, Maier & Neustadt, P.C.

(57) ABSTRACT

A thermal cycler is provided with a number of containing members 10 having a shape in conformity with a shape of micro tubes 6, nozzles 15 for jetting coolant to the respective containing members 10, a blower 5 for supplying the coolant to the nozzles 15, heaters 12 wound around the respective containing members 10, thermocouples 13 provided to be brought into contact with the respective containing members 10 and a control apparatus 14 for generating signals of the heaters 12 based on signals from the thermocouples 13 and outputting the generated signals. By carrying out independent temperature control for the respective micro tubes 6 by the control apparatus 14, accuracy of temperature control of the respective micro tubes 6 is promoted and the processing efficiency is promoted.

10 Claims, 20 Drawing Sheets

(a)

(b)

THERMAL CYCLER AND DNA AMPLIFIER METHOD

FIELD OF THE INVENTION

The present invention relates to a thermal cycler and a DNA amplifier method for amplifying nucleic acid of the DNA.

DESCRIPTION OF THE RELATED ART

In the case of inspecting how nucleic acid (gene) in a gene-recombinated crop influences on the human body or in the case of inspecting gene of a patient, the nucleic acid in the crop or nucleic acid particular to the patient must be extracted from respective individual. However, in order to provide nucleic acid of an amount necessary for inspection, extracted nucleic acid must be amplified and there is PCR (polymerase chain reaction) method as the amplifying method. The PCR method is featured in being highly accurate and highly reliable in order to directly analyze gene with less influence by heat.

According to PCR method known as a method of amplifying efficiently such a small amount of DNA (Deoxyribonucleic acid), one cycle is constituted by a step of denaturing DNA by maintaining a micro tube holding DNA at inside thereof at a temperature of around 95° C., a step of annealing DNA by maintaining DNA at a temperature of around 55° C. and a step of amplifying DNA by maintaining DNA at a temperature around 70° C. and DNA is amplified by repeating the cycle (refer to U.S. Pat. No. 4,683,202). In carrying out the PCR method, it is important to use an apparatus capable of controlling temperature with high accuracy since an efficiency of amplifying DNA is increased by accurately controlling the thermal cycle of the respective steps.

Further, as another amplifying method, there is known NASBA method in which nucleic acid is amplified at a constant temperature of 50 through 60° C.

However, highly accurate temperature control is needed even in NASBA method.

FIG. 1 shows a conventional example of thermal cycler which is an apparatus for automatically carrying out PCR method.

The thermal cycler is provided with a metal block 101 inserted with micro tubes 100, wells 102, a heater 103 and a cooling pipe 104.

The micro tubes 100 including a sample are inserted to the wells 102 engraved to the metal block 101 comprising aluminum and in the metal block 101, temperature of the micro tubes 100 is controlled by using the heater 103 and the cooling pipe 104 to thereby amplify DNA of the sample.

Normally, the wells 102 are formed at about one hundred portions in the metal block 101 and the micro tubes 100 of about one hundred pieces, are simultaneously processed.

Further, when DNA used for research is amplified, the kind of DNA is previously specified and therefore, an amount of about several microliters is sufficient, however, when unknown DNA used for inspection is amplified, an amount of about several milliliters is needed. Thereby, an enormous time period is taken for amplifying DNA to a desired amount.

However, in the above-described conventional apparatus, all of the micro tubes 100 of about one hundred pieces are simultaneously heated or cooled by the heater 103 and the cooling pipe 104 and therefore, it is difficult to uniformly control temperature. This is because temperature of the inserted micro tubes 100 (sample) is controlled by heating or cooling the metal block 101 inserted with the plurality of micro tubes 100. Therefore, there is a concern that temperature of the micro tubes 100 becomes nonuniform depending on positions of the metal block 101 and there is a possibility that an amount of product after reaction differs by the respective micro tubes 100 and becomes incomplete.

Further, individually different temperature control cannot be carried out for the respective micro tubes 100 and accordingly, for example, even when one hundred pieces thereof can be processed simultaneously, when the processing is started by inserting only ten pieces of the micro tubes 100 to be processed into the wells 102, the processing efficiency is lowered. Further, there poses a problem in which when the processing is on standby until one hundred pieces of the micro tubes 100 have been prepared, a time period of processing is increased.

SUMMARY OF THE INVENTION

Hence, the present invention has been carried out in view of the above-described conventional problem and it is an object of the present invention to provide a thermal cycler and a DNA amplifier in which highly accurate temperature control can be carried out with regard to individual micro tubes and the processing efficiency is promoted.

In order to achieve the above-described object, according to an aspect of the present invention, there is provided a thermal cycler comprising a plurality of wells capable of containing micro tubes holding a sample including nucleic acid, a plurality of heaters provided at the respective wells for directly or indirectly heating the micro tubes, a plurality of temperature sensors measuring temperature of the micro tubes, and a control apparatus inputted with measured values of the temperature sensors, supplying current to the plurality of heaters based on the measured values and controlling the temperature of the respective micro tubes independently from each other.

According to another aspect of the present invention, there is provided a thermal cycler comprising a plurality of wells capable of containing micro tubes holding a sample including nucleic acid, a plurality of nozzles provided at the respective wells jetting a medium to the wells, a plurality of heaters provided in the nozzles heating the medium, a plurality of temperature sensors measuring temperature of the micro tubes, and a control apparatus inputted with measured values of the temperature sensors, supplying current to the heaters based on the measured values and controlling the temperature of the respective micro tubes independently from each other.

According to another aspect of the present invention, there is provided a thermal cycler comprising a plurality of cylindrical wells which are capable of containing micro tubes holding a sample including nucleic acid, one end portion of each of which is formed with an opening portion for inserting the micro tube and other end portions of which constitute bottom portions, a plurality of temperature sensors installed in contact with outer walls of the wells measuring temperature of the micro tubes, a plurality of heaters arranged to surround the outer walls of the wells or proximately thereto heating the micro tubes, a case which is a case including a well chamber and an air chamber partitioned by a partition wall and in which the well chamber is arranged to align with the plurality of wells by protruding the opening portions of the wells to an outer side thereof and the outer walls of the wells having the temperature sensors to an inner side thereof and the air chamber includes a plurality of air fans, a plurality of cooling nozzles which are nozzles for cooling the micro tubes by jetting air to the wells, attached to be opposed to the bottom portions of the wells at positions of the partition wall in correspondence with the respective wells jetting air from the air chamber to the wells in the well chamber, and a control apparatus connected to the heaters, supplying current to the heaters in accordance with outputs of the temperature sensors controlling the temperature of the respective micro tubes independently from each other.

According to another aspect of the present invention, there is provided a thermal cycler comprising a plurality of wells capable of containing micro tubes holding a sample including nucleic acid and pasted with an indicator which differs in accordance with the respective sample, a plurality of pick up sensors detecting the indicator, a plurality of heaters provided at the respective wells directly or indirectly heating the micro tubes, a plurality of temperature sensors measuring temperature of the micro tubes, and a control apparatus inputted with measured values of the temperature sensors, supplying current to the heaters based on the measured values and controlling the temperature of the respective micro tubes independently from each other by a previously stored temperature pattern in correspondence with the indicator.

According to another aspect of the present invention, there is provided a DNA amplifier method having a control apparatus for controlling to heat a plurality of micro tubes holding a sample including nucleic acid independently from each other by a plurality of heat apparatus provided at the respective micro tubes based on measured values of a plurality of temperature sensors provided at the respective micro tubes and storing a temperature pattern heating the micro tubes, the DNA amplifier method comprising a step of reading the temperature pattern set for the respective micro tubes by the control apparatus, a step of generating a signal operating the heat apparatus based on the measured values and the temperature pattern by the control apparatus, a step of inputting the generated signal to the respective heat apparatus, heating the micro tubes independently from each other based on the signal by the heat apparatus and having a desired reaction carry out in the micro tubes, and a step of outputting a signal stopping operation of the heat apparatus to the heat apparatus based on the temperature pattern by the control apparatus.

According to another aspect of the present invention, there is provided a DNA amplifier method having a control apparatus controlling to heat a plurality of micro tubes for holding a sample including nucleic acid and pasted with an indicator which differs in accordance with the respective sample independently from each other by a plurality of heat apparatus provided at the respective micro tubes based on measured values of a plurality of temperature sensors provided at the respective micro tubes and storing a temperature pattern heating the micro tubes, the DNA amplifier method comprising a step of detecting the indicator and setting the temperature pattern in correspondence with the detected indicator by the control apparatus, a step of generating a signal operating the heat apparatus based on the measured values and the temperature pattern by the control apparatus, a step of inputting the generated signal to the respective heat apparatus, heating the micro tubes independently from each other based on the signal by the heat apparatus and having a desired reaction carry out in the micro tubes, and a step of outputting a signal for stopping operation of the heat apparatus to the heat apparatus based on the temperature pattern by the control apparatus.

DETAILED DESCRIPTION OF THE PREFERRED EMBODIMENTS

An explanation will be given as follows of embodiments of the invention in reference to the drawings.

First Embodiment

Figure 1:
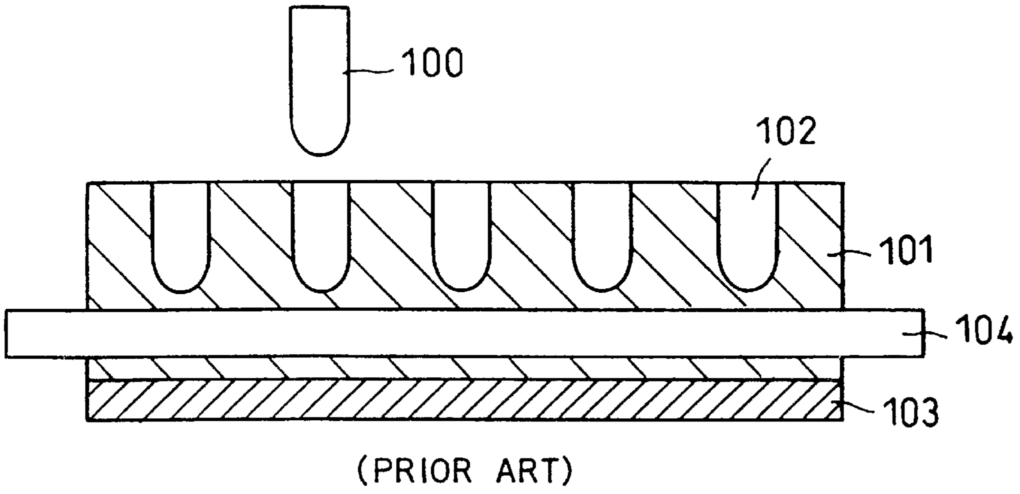
FIG. 1 is a longitudinal sectional view of a conventional thermal cycler.
Figure 2:
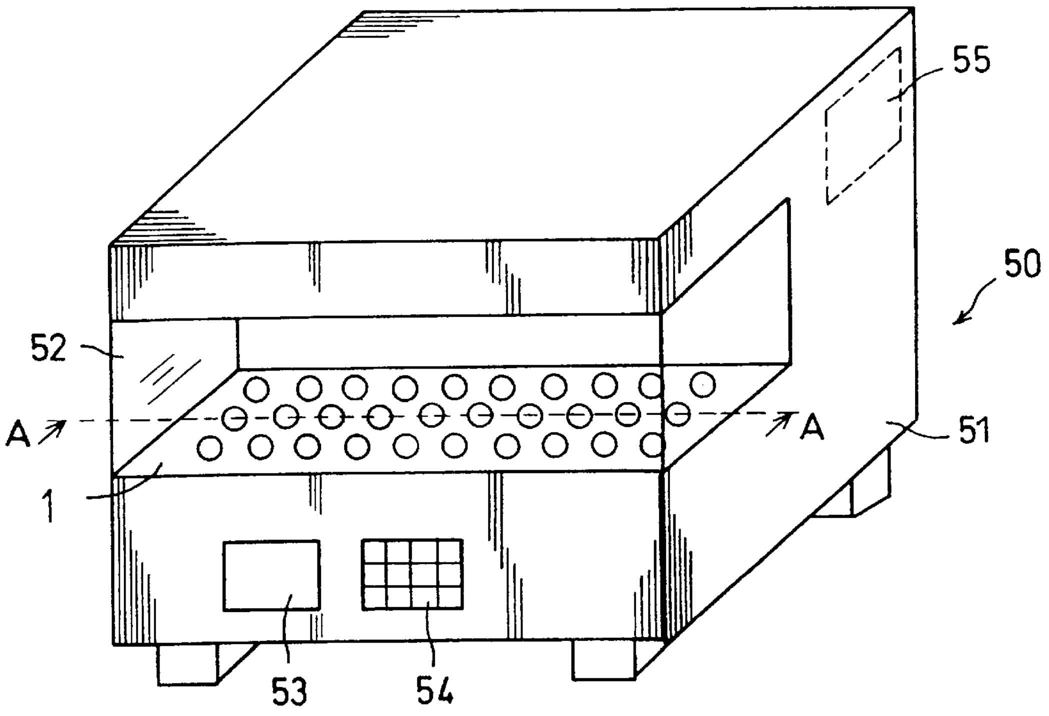
FIG. 2 is a perspective view of a thermal cycler according to the invention.

FIG. 2 is a perspective view of the thermal cycler. First, an explanation will be given of a thermal cycler apparatus 50 installed with a thermal cycler 1.

A thermal cycler 1 is built in a case 51. According to the thermal cycler 1, a portion of the case 51 is covered by a cover 52 having permeability such that a location of containing a plurality of micro tubes in the thermal cycler 1 (circle mark in FIG. 2) can optically be observed and the cover 52 can be opened and closed such that operation of inserting and taking out the micro tubes to and from the thermal cycler 1 can be carried out. Further, an outer surface of the case 51 is provided with a display panel 53 for displaying temperature and processing situation of respective micro tubes, presence or absence of the micro tubes and the like and an input unit 54 of ten keys or the like for inputting selection of temperature pattern set to the respective micro tubes or information of processing temperature or the like. Further, a control unit 55 for controlling the thermal cycler 1 is provided at inside of the case 51. The control unit 55 is connected to the thermal cycler 1, the display panel 53 and the input unit 54. Further, the control unit 55 may be an electronic device such as a personal computer provided outside of the case 51.

Nucleic acid in the example is amplified by heating or cooling a sample held in the micro tubes and including nucleic acid by the thermal cycler 50 having such a constitution.

An explanation will be given of the thermal cycler 1 as follows.

FIG. 3 through FIG. 6 show a first embodiment.

Figure 3:
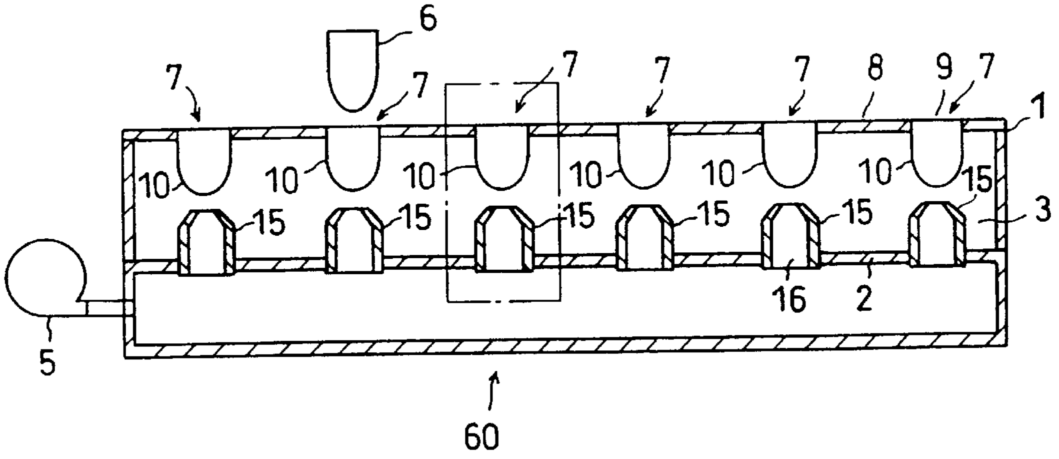
FIG. 3 is a longitudinal sectional view cutting FIG. 2 by a line A—A and viewing in an arrow mark direction.

FIG. 3 is a longitudinal sectional view cutting FIG. 2 by a line A—A and viewing in an arrow mark direction and is a constitution view of the first embodiment in which in the thermal cycler 1, the hollow case 1 comprising resin is divided into an upper chamber 3 (well chamber) and a lower chamber 4 (air chamber) by a partition wall 2. The lower chamber 4 constitutes a flow path of a coolant (for example, air). Further, an end portion of the lower chamber 4 is provided with an introducing port for introducing air to inside of the case 1 and the introducing port is connected with a blower 5 (air fan) for introducing air to inside of the case 1. In this case, air operates as a heat medium or a coolant.

A plurality of holes are perforated at a ceiling wall of the upper chamber 3. A number of the holes is, for example, about one hundred. The holes constitute wells 7 for containing micro tubes 6 and are arranged in a matrix shape or arranged concentrically at equal angular pitch when viewed from Z direction in FIG. 3.

The micro tube 6 is formed by a material having excellent heat conductivity such as a metal material in view of reducing heat transfer resistance. The material is, for example, iron, copper, aluminum, stainless steel or an alloy including one kind thereof In this case, the micro tube 6 is formed by press-molding a thin metal plate made of stainless steel. Further, an inner face portion of the micro tube 6 which is brought into contact with the sample held in the micro tube 6 is covered with a thin film inactive to the sample. The thin film is formed by coating, plating, painting or insert-molding.

Figure 4:
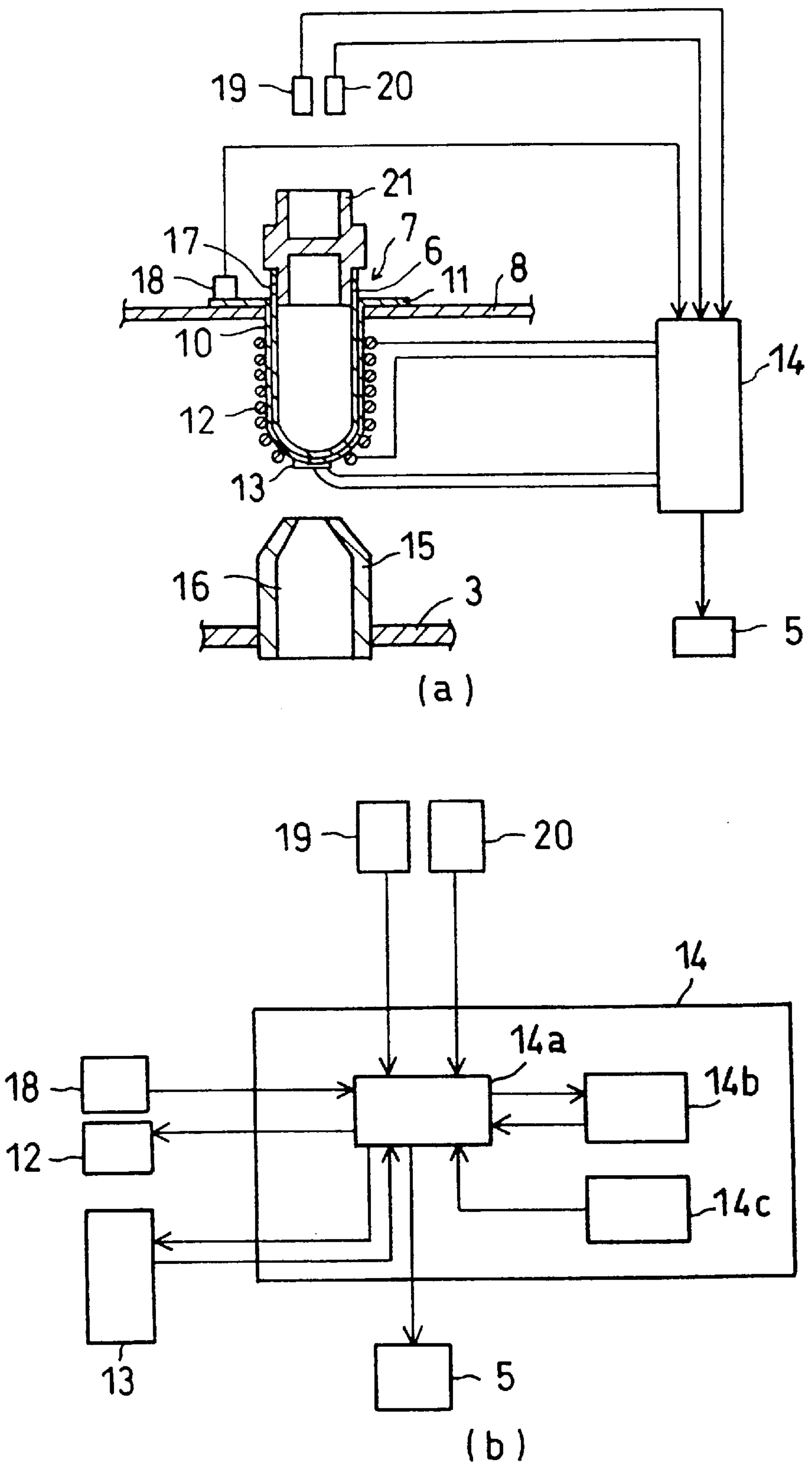
FIGS. 4(*a*) and 4(*b*) are longitudinal sectional views at a vicinity of a container according to a first embodiment of a thermal cycler of the invention.

Next, an explanation will be given of a constitution at a vicinity of the well 7 in reference to a longitudinal sectional view of FIG. 4(*a*) of the vicinity of the well 7 enlarging an area in FIG. 3 surrounded by one-dotted chain lines. Further, although in the following, an explanation will be given of one of the plurality of wells 7 provided at the upper chamber 3, others of the wells 7 are provided with quite the same constitution.

The well 7 is a substantially cylindrical containing member 10 having a shape protruded toward an inner side of the case 1 with a through hole 9 perforated at a ceiling 8 of the case 1 as its opening portion. A longitudinal section of the well 7 is provided with a shape substantially the same as that of a longitudinal section of the containing member 10. A front end of the protruded portion constituting one end of the containing member 10 is closed and a side of the through hole 9 constituting other end thereof is opened since the micro tube 6 is inserted thereinto. The containing member 10 is fixed to the ceiling 8 by a flange 11 provided at the containing member 10. Further, the containing member 10 is formed by a material the same as that of the micro tube 6. A shape of an inner face of the containing member 10 is formed by following a shape of an outer face of the micro tube 6 inserted into the containing member 10 and is formed such that the outer face of the micro tube 6 and the inner face of the containing member 10 are substantially brought into close contact with each other when the micro tub 6 is inserted into the containing member 10. Further, when the micro tube 6 and the containing member 10 are brought into close contact with each other, heat transfer resistance between the micro tube 6 and the containing member 10 is reduced. Further, the heat transfer resistance can further be reduced when the micro tube 6 is inserted thereinto while interposing grease or the like between the micro tube 6 and the containing member 10.

Further, an outer face of the containing member 10 is wound with a heater 12. The heater 12 is a heater comprising a metal wire of a nichrome wire or the like having high electric resistance. The heater 12 heats the micro tube 6 indirectly via the containing member 10.

Further, a thermocouple 13 is provided as a temperature sensor by being brought into contact with the outer face of a lower portion of the containing member 10.

The heater 12 and the thermocouple 13 are connected to a control apparatus 14. The control apparatus 14 is inputted with a measurement result from the thermocouple 13, generates a signal constituting a value of current conducted to the heater 12 based on the input value and outputs the signal to the heater 12.

Further, a nozzle 15 (cooling nozzle) is provided at a vicinity of the lower portion of the containing member 10. One end of the nozzle 15 is fixed to the partition wall 3 and other end thereof is arranged to jet air to the lower portion of the containing member 10. The nozzle 15 is fixed to the partition wall 3 to be fitted to a through hole 16 perforated at the partition wall 3. Air delivered from the lower chamber 5 is jetted to the micro tube 6 by passing through the nozzle 15. A sectional area of other end of the nozzle 15, that is, an area of an air jet port becomes smaller than a sectional area of one end thereof, that is, an area of the through hole 16. Further, the nozzle 15 is provided at the partition wall 3 opposed to a bottom portion of the containing member 10.

Further, the blower 5 is connected to the control apparatus 14 and the control apparatus 14 generates and outputs a control signal for controlling the blower 5 from a detection result of the thermocouple 13.

Further, an optical sensor 18 (indicator detecting sensor) for detecting an indicator 17 provided at the micro tube 6 is provided at a vicinity of the flange 11. An output of the optical sensor 18 is outputted to the control apparatus 14. Further, when the micro tube 6 and the containing member 10 are formed by a material having permeability, the optical sensor 18 may be provided inside of the upper chamber 3. However, in this case, a position of installing the indicator 17 is constituted by a portion of the micro tube 6 embedded into the upper chamber 3 when inserted into the upper chamber 3.

Further, there are provided an infrared temperature sensor 19 for measuring temperature of inside of the micro tube 6 and a luminance sensor 20 for measuring luminance of the inside of the micro tube 6. The infrared temperature sensor 19 and the luminance sensor 20 detect a state of the inside of the micro tube 6 via a cap 21 for closing the opening portion of the micro tube 6. In this case, the cap 21 is formed by a material having permeability. The infrared temperature sensor 19 and the luminance sensor 20 are provided above the cap 21 separately from the cap 21.

Next, an explanation will be given of the constitution of the control apparatus in reference to a block diagram of FIG. 4(*b*) of inside of the control apparatus 14.

The control apparatus 14 is provided with an operation unit 14*a*, a memory 14*b* and a timer 14*c*. The operation unit 14*a* is connected to the memory 14*b* and the timer 14*c*. The operation unit 14*a* is inputted with an output value from the thermocouple 13, an output value from the optical sensor 18, an output value from the infrared temperature sensor 19, an output value from the luminance sensor 20, data stored to the memory 14*b* and time from the timer 14*c*. Further, the operation unit 14*a* outputs a control signal for controlling the heater 12 to the heater 12 and a control signal for controlling the blower 5 to the blower 5. The memory 14*b* is stored with as data, temperature pattern set to the respective indicator, luminance (luminance value) of the sample, an output value (control signal) for controlling the heater 12 based on the temperature pattern and an output value (control signal) for controlling the blower 5 based on the temperature pattern. Further, the memory 14*b* outputs data read by the operation unit 14*a* to the operation unit 14*a*. Further, the timer 14*c* outputs elapse time to the operation unit 14*a*.

An explanation will be given of operation of the first embodiment comprising such a constitution.

Before explaining DNA amplifier, an explanation will be given here of a way of preparing the sample to be processed in the micro tube 6 and temperature of a nucleic acid processing.

First, the sample to be processed in the micro tube 6 is prepared by the following seven steps.

(1) Cells (the mucosa on an inner side of the cheek or the blood of a subject) having nucleic acid is put into a disinfected/sterilized beaker.

(2) Next, a reagent for dissolving protein of the cells is put into the beaker. At this occasion, DNA in double helix shape is separated and two pieces of DNA in a strip-like shape are constituted.

(3) Next, magnetic particles are put into the beaker after elapse of a constant time period of stirring.

(4) After a constant time period of stirring in the beaker, a buret is dipped into a liquid in the beaker, a magnet is arranged at an outer face of the buret and a constant amount of the liquid is taken into the buret. At this occasion, the magnetic particles are adhered to DNA in the strip-like shape and adsorbed to the magnet.

(5) Next, after closing an opening portion of the buret and separating the magnet from the buret, pure water is put into the buret. At this occasion, DNA is separated from the magnetic particles by the pure water.

(6) Next, the liquid in the buret is moved to a new beaker, a magnet is arranged again to an outer face of the beaker, only the magnetic particles are adsorbed thereto and the magnetic particles are taken out from the liquid in the beaker.

(7) Next, a pertinent amount of the liquid is moved from the beaker to the micro tube 6, the cap 21 is fitted to the opening portion of the micro tube 6 and the inside is hermetically closed. There are present a plurality of pieces of singles of DNA in the strip-like shape having no double helix structure at the inside portion.

In this way, there is prepared the sample including a plurality of singles of DNA in the strip-like shape in the pure water. Further, the above-described steps are carried out in a clean room under a constant temperature equal to or lower than room temperature. Further, the indicator 17 of sign/numeral/bar code is displayed at a predetermined position of the micro tube 6 by seal or print (ink jet) in order to identify what sample is put into the micro tube 6. Further, the sample can be prepared by carrying out the above-described operation (1) through (7) by a user or can be prepared by carrying out the above-described operation by a robot.

Figure 5:
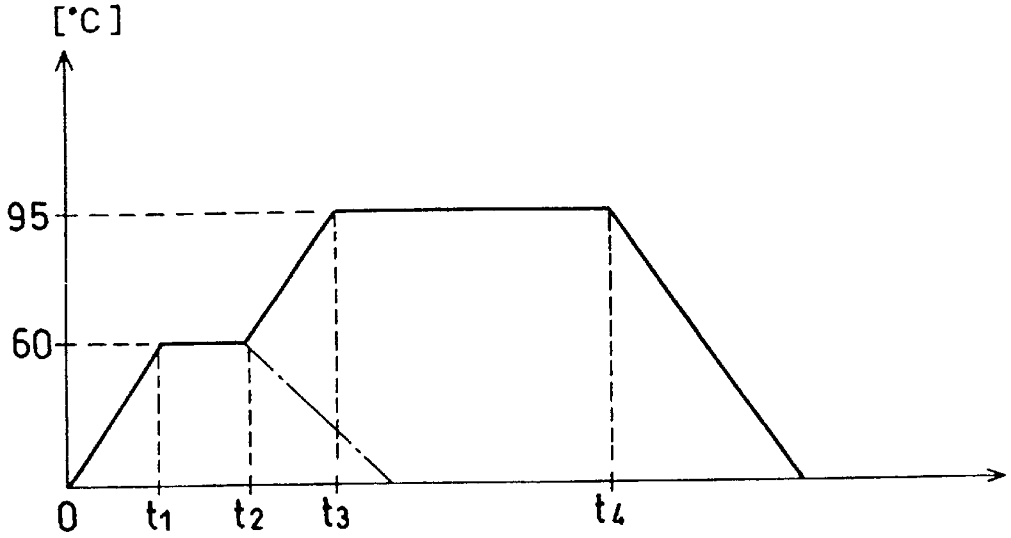
FIG. 5 is a diagram showing a relationship between time and temperature.

Next, an explanation will be given of nucleic acid processing pattern in reference to a diagram of FIG. 5 showing a relationship between time and temperature. In FIG. 5, the temperature is the result detected by the thermocouple 13 and the time is measured by the timer 14*c* built in the control apparatus 14.

(1) After inserting the micro tube 6 into the containing member 10, temperature of the sample in the micro tube 6 is elevated from room temperature to 60° C.

(2) Next, the temperature of the inside of the micro tube 6 is maintained at 60° C. for a predetermined time period (between t1 and t2). At a vicinity of 60° C., the single of DNA starts division and starts forming the double helix structure.

(3) Next, the luminance of the sample in the micro tube 6 is measured by the luminance sensor 20. When the measured luminance is equal to or lower than target luminance stored in the memory 14*b*, heating of the sample is stopped, the sample is cooled and the processing is finished (temperature follows one-dotted chain line from time t2 in FIG. 5).

(3) When the measure luminance is not equal to or lower than the target luminance, the temperature of the sample in the micro tube 6 is elevated to 95° C. (temperature follows bold line from time t2 in FIG. 5).

(4) Next, the temperature of the inside of the micro tube 6 is maintained at 95° C. for a predetermined time period (between t3 and t4). DNA which has been a single piece initially, becomes DNA substantially having the double helix structure.

(5) Next, the temperature of the sample of the inside of the micro tube 6 is lowered to room temperature. After reaching room temperature, the micro tube 6 is taken out from the containing member 10.

Further, the above-described temperature pattern is previously stored to the memory 14*b* in the control apparatus 14 and PI control or PID control is carried out by a measured value of the thermocouple 13 and along the stored temperature pattern. Further, there is a case in which the temperature pattern differs depending on the kind of the sample or how the processing is carried out. Further, the temperature of the sample is a temperature substantially coinciding with the temperature of the micro tube 6.

Figure 6:
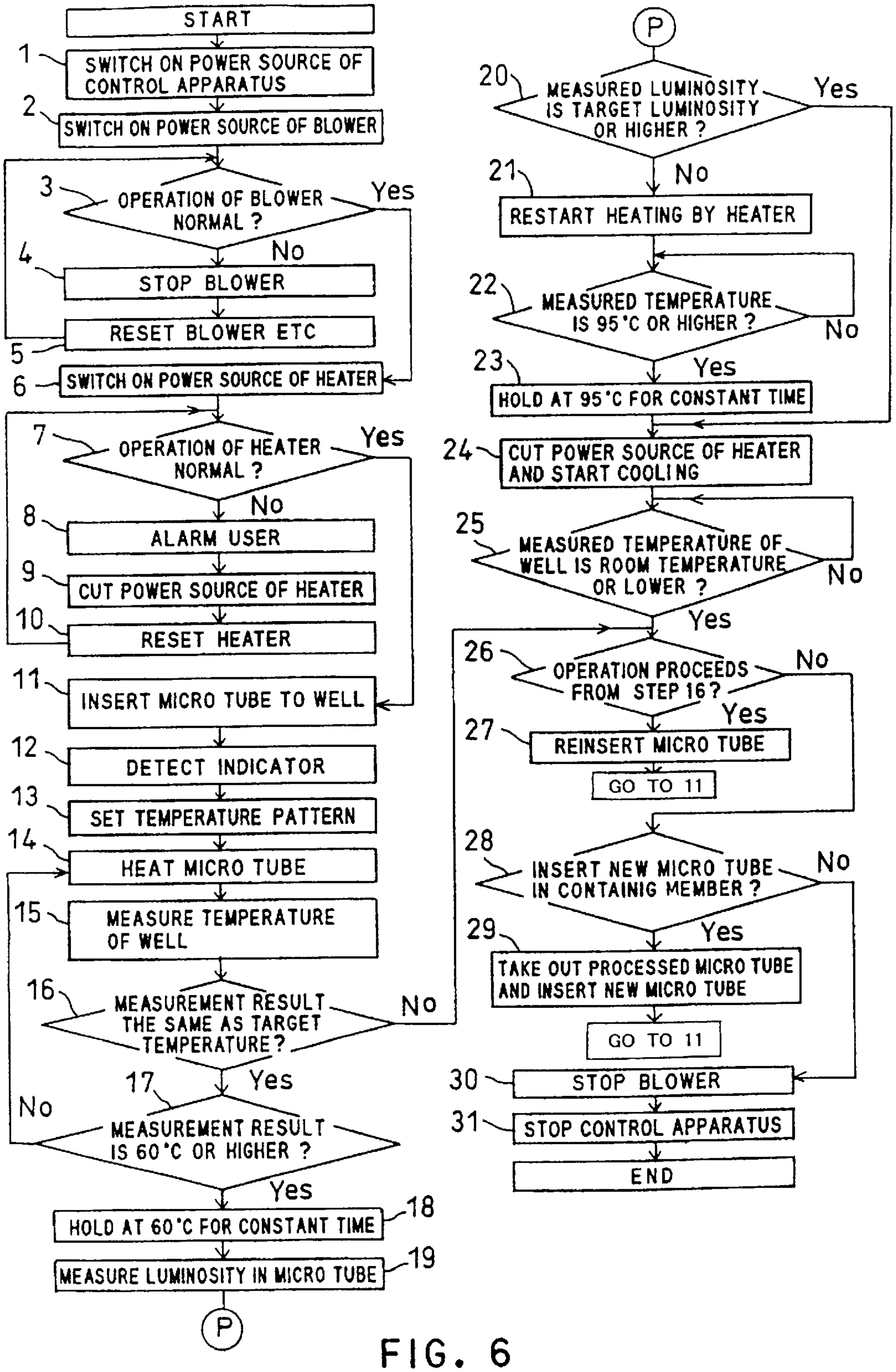
FIG. 6 is a flowchart of the first embodiment of the DNA amplifier method according to the invention.

Next, an explanation will be given of the processing method in reference to the flowchart of FIG. 6 as follows.

(1) Power source of the control apparatus 14 is switched on. The measurement result from the thermocouple 13 is stored to the memory 13*b* as initial temperature of the micro tube 6.

(2) Main power source of the blower 5 is switched on and air is introduced into the lower chamber 4. The control signal for controlling the blower 5 is outputted from the operation unit 14*a*.

(3) After elapse of a constant time period, whether the blower 5 is normally operated is confirmed. When the measurement result from the thermocouple 13 after elapse of the constant time period is lower than initial temperature, no problem is posed and the operation proceeds to (6). When the measurement result is higher than the initial temperature, the operation proceeds to (4). The measurement result of the thermocouple 13 is inputted to the operation unit 14*a* and the initial temperature stored to the memory 14*b* is read by the operation unit 14*a* and is compared with the measurement result.

(4) When the measurement result is higher than the initial temperature, the blower 5 is stopped. A control signal of stopping the blower 5 is outputted from the operation unit 14*a*.

(5) A state of connecting the blower 5 and the lower chamber 4, or whether the nozzle 15 is clogged by dust or the like is investigated and the setting is executed again. The operation proceeds to (3).

(6) When the measurement result is lower than the initial temperature, the power source of the heater 12 is switched on. Although a control signal for controlling the heater 12 is to be outputted from the operation unit 14*a*, at the current time point, the control signal is not outputted.

(7) After elapse of a constant time period, whether the thermocouple 13 and the heater 12 are normally operated is confirmed. When the thermocouple 13 and the heater 12 are operated normally, the operation proceeds to (11). When the normal operation is not carried out, the operation proceeds to (8). At this stage, although power source of the heater 12 is switched on, the control signal for controlling the heater 12 is not outputted from the control apparatus 14 and therefore, the measurement result of the thermocouple 13 is around room temperature and a case in which the measurement result is temperature around the room temperature is determined as normal. The measurement result of the thermocouple 13 is inputted to the operation unit 14*a* and is compared with an output value of the thermocouple 13 at room temperature stored to the memory 14*b*.

(8) When the thermocouple 13 and the heater 12 are not operated normally, the user is alarmed by sound, light or the like. In alarming, a signal for emitting sound or a signal for emitting light is outputted from the operation unit 14*a*.

(9) The user cuts the power source of the heater 12.

(10) After elapse of a constant time period, the user investigates the state of the heater 12 or a state of connecting the heater 12 with the control apparatus 14 and resets the heater 12. The operation proceeds to (6).

(11) When the thermocouple 13 and the heater 12 are operated normally, the cover 52 is opened and the micro tubes 6 are inserted into the respective wells 7. After inserting thereof, the cover 52 is closed. The operation of opening and closing the cover 52 and inserting and taking out the micro tubes 6 may be carried out by an operational robot. Further, the micro tubes 6 are arranged at positions where the indicators 17 can be detected by the optical sensor 18.

(12) The indicators 17 are detected by the optical sensor 18 and a detection result is outputted to the control apparatus 14. The detection result from the optical sensor 18 is inputted to the operation unit 14*a*.

(13) The operation unit 14*a* extracts the temperature pattern in correspondence with the indicator inputted from the memory 14*b* at inside of the control apparatus 14. In accordance with the extracted temperature pattern, the control signal is outputted to the heater 12 and heating of the micro tubes 6 is started.

(14) In accordance with the control signal from the operation unit 14*a*, current is conducted to the heater 12. The containing member 10 is heated by Joule's heat generated by the heater 12 after conducting current. Further, simultaneously with starting the heating operation, initial time of the timer 14*c* is set to 0. Further, with respect to the sample in the micro tube 6, the micro tube 6 is heated by transferring heat to the sample in the micro tube 6 by heating the containing member 10 and the sample is heated by transferring heat by heating the micro tube 6.

(15) The measurement result by the thermocouple 13 is inputted to the operation unit 14*a*.

(16) The measurement result inputted by the operation unit 14*a* and target temperature with respect to elapse time period stored to the memory 14*b* are compared with each other by the operation unit 14*a* and when the measurement result is substantially the target temperature (within allowable range), the operation proceeds to (17) and when the measurement result is out of the allowable range, the operation proceeds to (24). When the operation proceeds to (24), it is regarded that the micro tube 6 is not inserted into the containing member 10 in a desired state and insertion of the micro tube 6 is executed again.

(17) When the measurement result falls substantially in the allowable range of the target temperature, the operation unit 14*a* successively determines whether the measurement result is equal to or higher than 60° C. or lower than 60° C. When the measurement result is equal to or higher than 60° C., the operation proceeds to (18) and the operation proceeds to (14) when the measurement result is lower than 60° C.

(18) When the measurement result is equal to or higher than 60° C., the micro tube 6 is maintained at temperature of 60° C. for a constant period of time. At this occasion, the operation unit 14*a* keeps outputting a control signal to the heater 12 in correspondence with the measurement result of the thermocouple 13 until elapse of hold time period based on the temperature pattern read from the memory 14*b*. Further, measurement of time is carried out by the timer 14*c* and is outputted to the operation unit 14*a* as needed.

(19) Next, a signal of having the luminance sensor 20 measure the luminance of the sample in the micro tube 6 is outputted from the operation unit 14*a* to the luminance sensor 20 and based on the signal, measurement result of the luminance sensor 20 is inputted to the operation unit 14*a*.

(20) The operation unit 14*a* compares the measured luminance with target luminance stored to the memory 14*b*. When the measurement result is equal to or lower than the target luminance, the operation proceeds to (24) and proceeds to (21) otherwise.

Further, when the measured luminance is substantially the same as the target luminance, it is regarded that the double helix structure is formed in DNA and it is determined that DNA has not formed with the double helix structure yet when the measured luminance is larger than the target luminance. This is because the luminance is lowered since a single piece of DNA is divided to form the double helix structure by elevating the temperature of the sample to be equal to or higher than 60° C. (21) When the measured luminance is not equal to or lower than the target luminance, a control signal is outputted from the operation unit 14*a* to the heater 12 and current is flowed to the heater 12 in accordance with the control signal and the micro tube 6 is heated by generating Joule's heat of the heater 12.

(22) Next, the operation unit 14*a* determines whether the measurement result of the thermocouple 13 exceeds 95° C. by the measurement result of the thermocouple 13. When the measurement result exceeds 95° C., the operation proceeds to (23) and when the measurement result does not exceed 95° C., the operation proceeds to (21).

(23) When the measurement result exceeds 95° C., the temperature of the micro tube 6 is maintained at 95° C. for a constant time period. It is regarded that by holding temperature of the inside of the micro tube 6 at 95° C., DNA is determined to be divided to constitute the double helix structure. The heater 12 is outputted with a control signal generated based on the temperature pattern in the memory 14*b* and the measurement result from the thermocouple 13 from the operation unit 14*a*. In accordance with the control signal, current is conducted to the heater 12. Further, time is measured by the timer 14*c* with time point at which temperature exceeds 95° C. as 0 and is outputted to the operation unit 14*a* as needed. The operation proceeds to (24).

(24) When the measured temperature is equal to or lower than the target temperature, or when the operation proceeds from (23), the temperature of the micro tube 6 is lowered to room temperature by jetting air introduced to the lower chamber 4 from the nozzle 15 to the containing member 10. Further, the operation unit 14*a* outputs a control signal for setting current conducted to the heater 12 to 0.

(25) It is determined whether the temperature of the micro tube 6 is equal to or lower than room temperature. The measurement result of the thermocouple 13 is inputted to the operation unit 14*a* and the operation unit 14*a* determines whether the measurement result is equal to lower than room temperature. When the measurement result of the thermocouple 13 is equal to or lower than room temperature, the operation proceeds to (26) and when the measurement result is higher than room temperature, the operation proceeds to (24) and cooling of the micro tube 6 is continuously carried out.

(26) The operation unit 14*a* determines whether the operation proceeds to (26) since the measurement result and the target temperature do not coincide with each other in (16) or whether the operation proceeds to (26) since the measurement result is equal to or lower than room temperature at (25). When the operation proceeds from (16), the operation proceeds to (27) and otherwise, the operation proceeds to (28).

(27) When the operation proceeds from (16), the operation proceeds to (11) to execute again insertion of the micro tube 6 into the containing member 10. The operation unit 14*a* stores to the memory 14*b*, data that a micro tube has not yet been inserted into the containing member 10 which has been inserted with the micro tube 6 which is to be taken out.

(28) When the operation proceeds from (25), the operation unit 14*a* determines whether a new one of the micro tube 6 is to be inserted into the containing member 10. There is a case in which the memory 14*b* is previously stored with a number of pieces to be processed and there is a case in which the user inputs newly whether a new one of the micro tube 6 is present. When there is the micro tube 6 which has not been processed and the processing is to be carried out continuously, the operation proceeds to (29) and when the processing is to be finished, the operation proceeds to (30).

(29) When the processing is to be carried out continuously, the micro tube 6 which has been processed is taken out from the containing member 10 and a new one of the micro tube 6 is inserted thereinto. After inserting the micro tube 6 which has not been processed into the containing member 10, the operation proceeds to (12).

(30) When the processing is not to be carried out continuously, a control signal for stopping the blower 5 is outputted from the operation unit 14*a* and the blower 5 is stopped. Thereafter, the main power source of the blower 5 is cut.

(31) The power source of the control apparatus 14 is cut.

By, the above-described steps, nucleic acid is amplified and DNA having the double helix structure is provided from single pieces of DNA in the sample.

According to the first embodiment as mentioned above, by providing the heater 12 and the thermocouple 13 to the respective containing member 10, independent temperature control can be carried out for the respective micro tube 6 by the control apparatus 14, it is not necessary for a plurality of the micro tubes 6 to process simultaneously and similarly, and the respective micro tubes 6 can be processed by different temperature patterns or different start time. In other words, when there are, for example, one hundred pieces of the containing members 10, it is not necessary for the processing to be on standby until the one hundred pieces of the micro tubes 6 have been prepared and the time period until finishing the processing can be shortened. Further, after the micro tube 6 in which the sample is held has been prepared, nudeic acid processing can be carried out and accordingly, the processing start time can be made to differ for the respective micro tube 6 and the processing efficiency can be promoted. Further, the micro tubes 6 having different temperature patterns can also be processed simultaneously or with different processing start time.

Further, the micro tube 6 and the containing member 10 are arranged to be substantially brought into close contact with each other and therefore, heat transfer resistance from the heater 12 to the sample in the micro tube 6 can be reduced and response of temperature control can be promoted.

Further, air is always jetted from the nozzle 15 to the containing member 10 and therefore, influence by radiation heat from other containing member 10 can be restrained and temperature control for heating can be carried out with high accuracy. Further, cooling time of the micro tube 6 can be shortened.

Further, when the measurement result of the infrared temperature sensor 19 inputted to the operation unit 14*a* is used, the temperature control can be carried out with higher accuracy.

Second Embodiment

Figure 7:
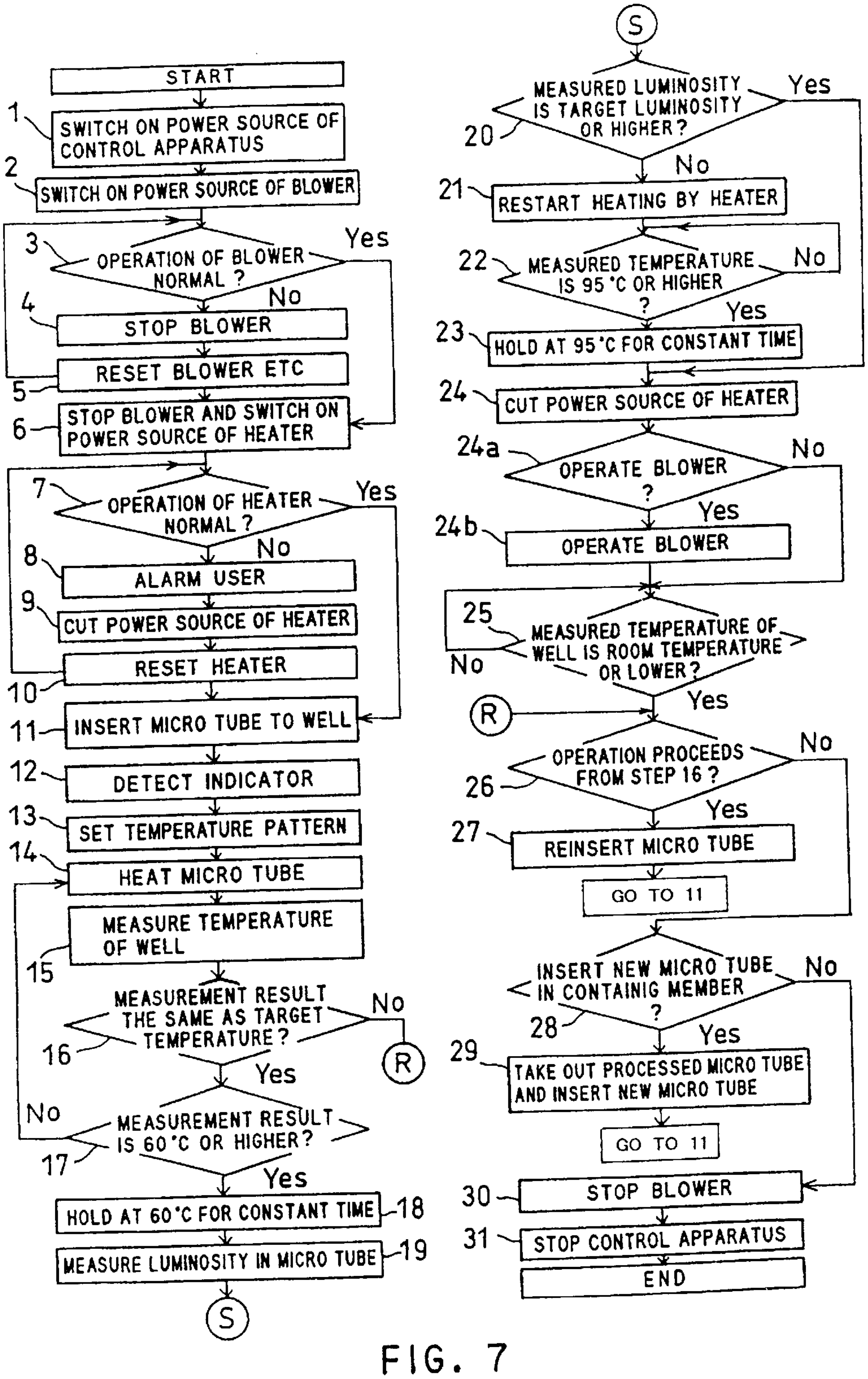
FIG. 7 is a flowchart of a second embodiment of a DNA amplifier method according to the invention.

Next, an explanation will be given of a second embodiment of the present invention in reference to FIG. 7.

Further, in the following respective embodiments, the same constituent elements are attached with the same notations and a duplicated explanation thereof will be omitted.

According to the second embodiment, the containing member 10 is not always jetted with air from the nozzle 15.

Further, the constitution of the second embodiment is the same as that of the first embodiment.

An explanation will be given of a processing method of the second embodiment in reference to FIG. 7.

(1) Power source of the control apparatus 14 is switched on. The measurement result from the thermocouple 13 is stored to the memory 13(*b*) as initial temperature of the micro tube 6.

(2) Main power source of the blower 5 is switched on. A control signal for controlling the blower 5 is outputted from the operation unit 14*a*.

(3) After elapse of a constant time period, whether the blower 5 is normally operated is confirmed. When the measurement result from the thermocouple 13 after elapse of the constant time period is lower than the initial temperature, no problem is posed and the operation proceeds to (6). When the measurement result is higher than the initial temperature, the operation proceeds to (4). The measurement result of the thermocouple 13 is inputted to the operation unit 14*a* and the initial temperature stored to the memory 14*b* is read by the operation unit 14*a* and is compared with the measurement result.

(4) When the measurement result is higher than the initial temperature, the blower 5 is stopped. A control signal of stopping the blower 5 is outputted from the operation unit 14*a*.

(5) A state of connecting the blower 5 and the lower chamber 4 or whether the nozzle 15 is clogged by dust or the like is investigated and the setting is carried out again. The operation proceeds to (3).

(6) When the measurement result is lower than the initial temperature, a control signal for stopping the blower 5 is outputted from the operation unit 14*a* and the blower 5 is stopped in accordance with the control signal. Successively, power source of the heater 12 is switched on. Although a control signal for controlling the heater 12 is to be outputted from the operation unit 14*a*, at the current time point, the control signal is not outputted.

(7) After elapse of a constant time period, whether the thermocouple 13 and the heater 12 are normally operated is confirmed. When the thermocouple 13 and the heater 12 are operated normally, the operation proceeds to (11). When the normal operation is not carried out, the operation proceeds to (8). At this stage, although power source of the heater 12 is switched on, the control signal for controlling the heater 12 is not outputted and accordingly, measurement result of the thermocouple 13 is about room temperature and a case in which the measurement result is temperature around the room temperature is determined as normal. The measurement result of the thermocouple 13 is inputted to the operation unit 14*a* and is compared with an output value of the thermocouple 13 at room temperature stored to the memory 14*b*.

(8) When the thermocouple 13 and the heater 12 are not operated normally, the user is alarmed by, sound, light or the like. In alarming, a signal for emitting sound or a signal for emitting light is outputted from the operation unit 14*a*.

(9) The user cuts the power source of the heater 12.

(10) After elapse of a constant time period, the user investigates a state of the heater 12 or a state of connecting the heater 12 with the control apparatus 14 and resets the heater 12. The operation proceeds to (6).

(11) When the thermocouple 13 and the heater 12 are operated normally, the cover 52 is opened and the micro tubes 6 are inserted into the respective wells 7. After inserting thereof, the cover 52 is closed. The operation of opening and dosing the cover 52 and inserting and taking out the micro tubes 6 may be carried out by an operational robot. Further, the micro tubes 6 are arranged at positions where the indicators 17 can be detected by the optical sensor 18.

(12) The indicators 17 are detected by the optical sensor 18 and a detection result is outputted to the control apparatus 14. The detection result from the optical sensor 18 is inputted to the operation unit 14*a*.

(13) The operation unit 14*a* extracts a temperature pattern in correspondence with the inputted indicator from the memory 14*b* at inside of the control apparatus 14. In accordance with the extracted temperature pattern, the control signal is outputted to the heater 12 and heating of the micro tube 6 is started.

(14) Current is conducted to the heater 12 in accordance with the control signal from the operation unit 14*a*. The containing member 10 is heated by Joule's heat generated by the heater 12 after conducting current. Further, simultaneously with starting the heating operation, initial time of the timer 14*c* is set to 0. Further, with respect to the sample in the micro tube 6, by heating the containing member 10, heat is transferred and the micro tube 6 is heated and by heating the micro tube 6, heat is transferred and the sample is heated.

(15) Measurement result by the thermocouple 13 is inputted to the operation unit 14*a*.

(16) The measurement result inputted to the operation unit 14*a* and target temperature with respect to elapse time stored to the memory 14*b* are compared with each other by the operation unit 14*a*, when the measurement result is substantially the target temperature (within allowable range), the operation proceeds to (17) and when the measurement result is out of the allowable range, the operation proceeds to (24). When the operation proceeds to (24), it is regarded that the micro tube 6 is not inserted into the containing member 10 in a desired state and insertion of the micro tube 6 is carried out again.

(17) When the measurement result is substantially within the allowable range of the target temperature, the operation unit 14*a* successively determines whether the measurement result is equal to or higher than 60° C. or lower than 60° C. When the measurement result is equal to or higher than 60° C., the operation proceeds to (18) and when the measurement result is lower than 60° C., the operation proceeds to (14).

(18) When the measurement result is equal to or higher than 60° C., the micro tube 6 is maintained at temperature of 60° C. for a constant time period. At this occasion, the operation unit 14*a* keeps outputting the control signal to the heater 12 in correspondence with the measurement result of the thermocouple 13 until elapse of hold dime period based on the temperature pattern read from the memory 14*b*. Further, measurement of time is carried out by the timer 14*c* and is outputted to the operation unit 14*a* as necessary.

(19) Next, a signal of having the luminance sensor 20 measure the luminance of the sample in the micro tube 6 is outputted from the operation unit 14*a* to the luminance sensor 20 and based on the signal, measurement result of the luminance sensor 20 is inputted to the operation unit 14*a*.

(20) The operation unit 14*a* compares the measured luminance with target luminance stored to the memory 14*b*. When the measurement result is equal to or lower than the target luminance, the operation proceeds to (24) and otherwise, the operation proceeds to (21).

Further, when the measured luminance is substantially the same as the target luminance, it is regarded that the double helix structure is formed in DNA and when the measured luminance is larger than the target luminance, it is determined that DNA has not yet formed with the double helix structure. This is because the luminance is lowered since a single piece of DNA is divided to form the double helix structure by elevating the temperature of the sample to about 60° C. or higher.

(21) When the measured luminance is not equal to or lower than the target luminance, a control signal is outputted from the operation unit 14*a* to the heater 12 and in accordance with the control signal, current is flowed to the heater 12 and the micro tube 6 is heated by Joule's heat of the heater 12.

(22) Next, the operation unit 14*a* determines whether the measurement result of the thermocouple 13 exceeds 95° C. from the measurement result of the thermocouple 13. When the measurement result exceeds 95° C., the operation proceeds to (23) and when the measurement result does not exceed 95° C., the operation proceeds to (21).

(23) When the measurement result exceeds 95° C., the temperature of the micro tube 6 is maintained at 95° C. for a constant time period. It is determined that by maintaining the temperature of inside of the reaction tube 6 at 95° C., DNA is divided to constitute the double helix structure. The heater 12 is outputted with a control signal generated based on the temperature pattern in the memory 14*b* and the measurement result from the thermocouple 13 from the operation unit 14*a*. In accordance with the control signal, current is conducted to the heater 12. Further, time is measured by the timer 14*c* with time point exceeding 95° C. as 0 and is outputted to the operation unit 14*a* as necessary. The operation proceeds to (24).

(24) When the measured temperature is equal to or lower than the target temperature or when the operation proceeds from (23), the operation unit 14*a* outputs a control signal for setting current conducted to the heater 12 to 0 and heating by the heater 12 is stopped.

(24*a*) Whether the micro tube 6 is to be cooled by operating the blower 5 is determined.

When there is the micro tube 6 which has not been processed yet in a number of pieces of the micro tubes 6 to be processed which are previously stored to the memory 14*b*, the operation unit 14*a* proceeds to (24*b*) for starting forced air cooling by operating the blower 5 and the operation proceeds to (25) when the forced air cooling is not necessary.

(24*b*) When the forced air cooling is necessary, the operation unit 14*a* generates a control signal for operating the blower 5 and in accordance with the control signal, the blower 5 starts operating. By operating the blower 5, air is introduced to the lower chamber 4, air is jetted from the nozzle 15 to the containing member 10 and lowers temperature of the micro tube 6 to room temperature.

Further, when air is jetted to a single one of the micro tubes 6, air is jetted from all of the nozzles 15 to the respective micro tubes 6, and accordingly, even other micro tubes 6 which are not needed to be cooled are heated. The operation unit 14*a* outputs the control signal to the blower 5 and generates and outputs new control signals to the respective heaters 12 for heating the other micro tubes 6. The control signal outputted to the heater 12 is a control signal canceling the cooling operation by air jetted from the nozzle 15 and is set to a value larger than a value of current conducted before jetting air.

(25) Whether the temperature of the micro tube 6 is equal to or lower than room temperature is determined. The measurement result of the thermocouple 13 is inputted to the operation unit 14*a* and whether the measurement result of the operation unit 14*a* is equal to or lower than room temperature is determined. When the measurement result of the thermocouple 13 is equal to or lower than room temperature, the operation proceeds to (26) and when the measurement result is higher than room temperature, the operation proceeds to (24) and cooling of the micro tube 6 is continuously carried out.

(26) The operation unit 14*a* determines whether the operation proceeds to (26) since the measurement result and the target temperature do not coincide with each other at (16) or whether the operation proceeds to (26) since the measurement result is equal to or lower than room temperature (25). When the operation proceeds from (16), the operation proceeds to (27) and otherwise, the operation proceeds to (28).

(27) When the operation proceeds to (27) from (16), the operation proceeds to (11) to carry out insertion of the micro tube 6 into the containing member 10 again. The operation unit 14*a* stores to the memory 14*b*, data that a micro tube has not yet been inserted into the containing member 10 which has been inserted with the micro tube 6 which is to be taken out.

(28) When the operation proceeds from (25), the operation unit 14*a* determines whether a new one of the micro tube 6 is to be inserted into the containing member 10. There is a case in which the memory 14*b* is previously stored with a number of pieces to be processed and there is a case in which the user newly inputs whether there is a new one of the micro tube 6. When there is the micro tube 6 which has not been processed and the processing is to be carried out continuously, the operation proceeds to (29) and when the processing is to be finished, the operation proceeds to (30).

(29) When the processing is to be carried out continuously, the micro tube 6 which has been processed is taken out from the containing member 10 and a new one of the micro tube 6 is inserted. After inserting the micro tube 6 which has not been processed into the containing member 10, the operation proceeds to (12).

(30) When the processing is not to be carried out continuously, the main power source of the blower 5 is cut.

(31) The power source of the control apparatus 14 is cut.

By the above-described steps, nucleic acid is amplified and DNA having the double helix structure is provided from single pieces of DNA in the sample.

According to the second embodiment as mentioned above, independent temperature control can be carried out for the respective micro tube 6 by the control apparatus 14 by providing the heater 12 and the thermocouple 13 to the respective containing member 10.

Further, air for cooling the micro tube 6 can be jetted as necessary. For example, when there is the micro tube 6 which is on standby for processing, air is injected from the nozzle 15 to the micro tube 6 and when there is not the micro tube 6 which is on standby for processing, air is injected from the nozzle 15 to the micro tube 6. By operating in this way, power consumption can be reduced and sound emitted by flowing air can be reduced.

Third Embodiment

Next, an explanation will be given of a constitution of a third embodiment of the invention in reference to FIG. 8 as follows.

The feature of the third embodiment resides in that the blower 5 is provided to the respective micro tube 6.

Figure 8:
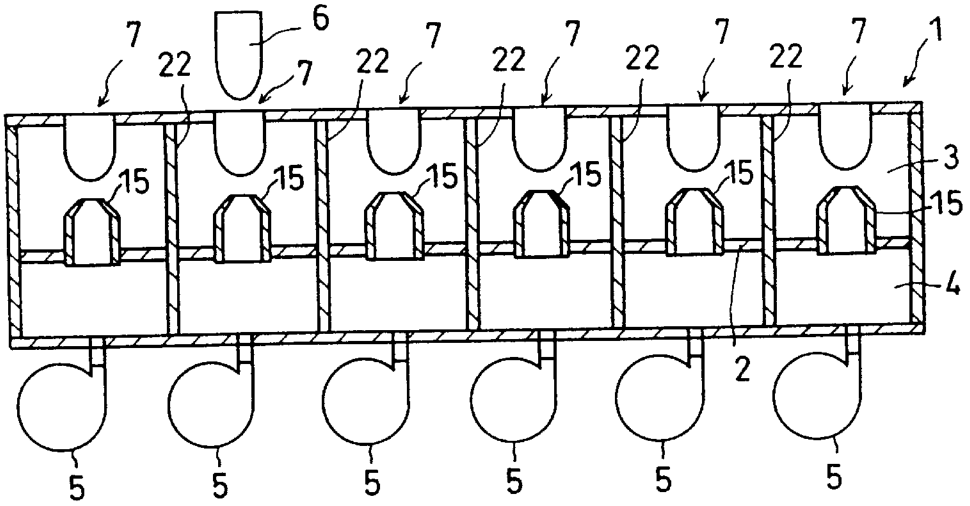
FIG. 8 is a longitudinal sectional view of a case of a third embodiment of a thermal cycler according to the invention.

FIG. 8 is a longitudinal sectional view of the case 1 according to the third embodiment in which there are provided dividing plates 22 for dividing the case 1 substantially in the vertical direction for the respective micro tubes 6 and the blowers 5 are connected to the lower chambers 4 divided by the dividing plates 22. That is, the heater 12 and the blower 5 are provided to a single one of the micro tube 6.

According to such a constitution, heating or cooling can be controlled for the respective micro tubes 6 and by providing the blowers 5 for the respective micro tubes 6, all the micro tubes 6 can be supplied with air having substantially uniform temperature and flow rate. Therefore, highly accurate temperature control can be carried out.

Fourth Embodiment

Next, an explanation will be given of constitution of a fourth embodiment of the invention in reference to FIG. 9.

The feature of the fourth embodiment resides in that the containing member 10 is formed by a metal having high electric resistance and heat is generated by conducting current to the containing member 10.

Figure 9:
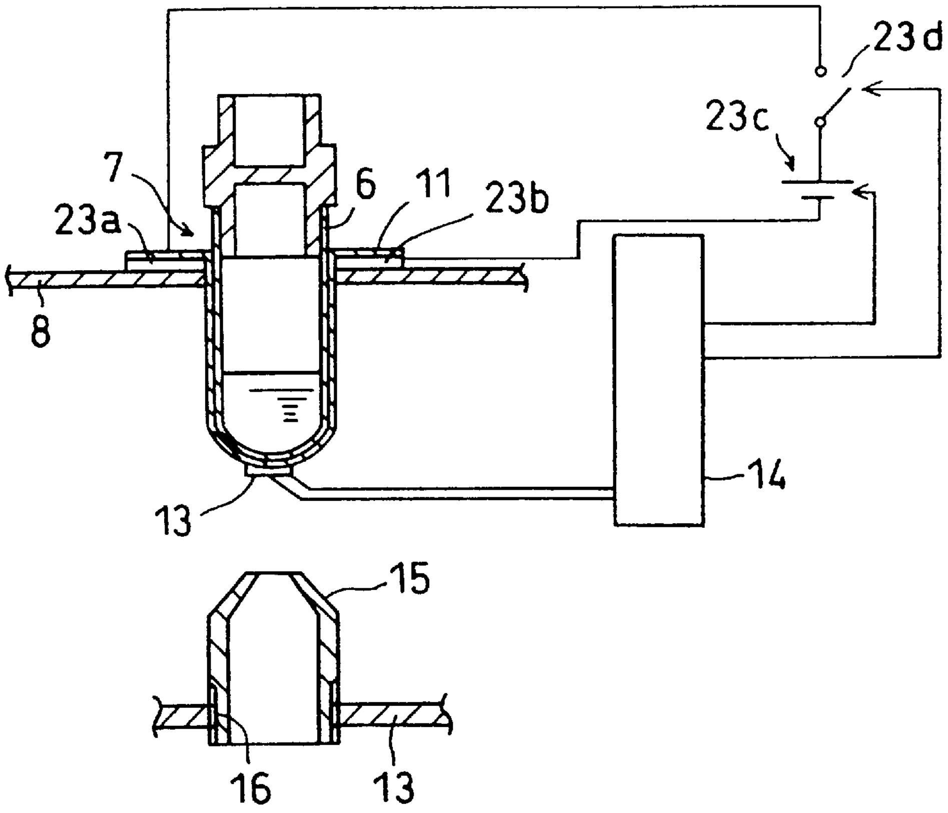
FIG. 9 is a longitudinal sectional view of a vicinity of a container of a fourth embodiment of a thermal cycler according to the invention.

FIG. 9 is a longitudinal sectional view of a vicinity of the containing member 10 and the nozzle according to the fourth embodiment and the containing member is formed by nickel, chromium, bismuth, chromel P, inver or an alloy including at least one kind of these. Terminals 23*a* and 23*b* are arranged between the flange 11 and the ceiling 8 to be brought into contact with each other. The terminals 23*a* and 23*b* constitute a closed circuit by a power source 23*c* and a switch 23*d*. The control apparatus 14 controls voltage (current) supplied from the power source 23*c* and ON/OFF of the switch 23*d* based on the measurement result of the thermocouple 13.

Voltage is applied between the terminals 23*a* and 23*b* and current is conducted to the containing member 10. By conducting current, the containing member 10 generates Joule's heat to thereby heat the micro tube 6.

According to the fourth embodiment, the heat apparatus can be constituted by a simple constitution.

Fifth Embodiment

Next, an explanation will be given of constitution of a fifth embodiment of the invention in reference to FIG. 10.

The feature of the fifth embodiment resides in that the nozzle 15 is extended to cover an outer peripheral face of the containing portion 10.

Figure 10:
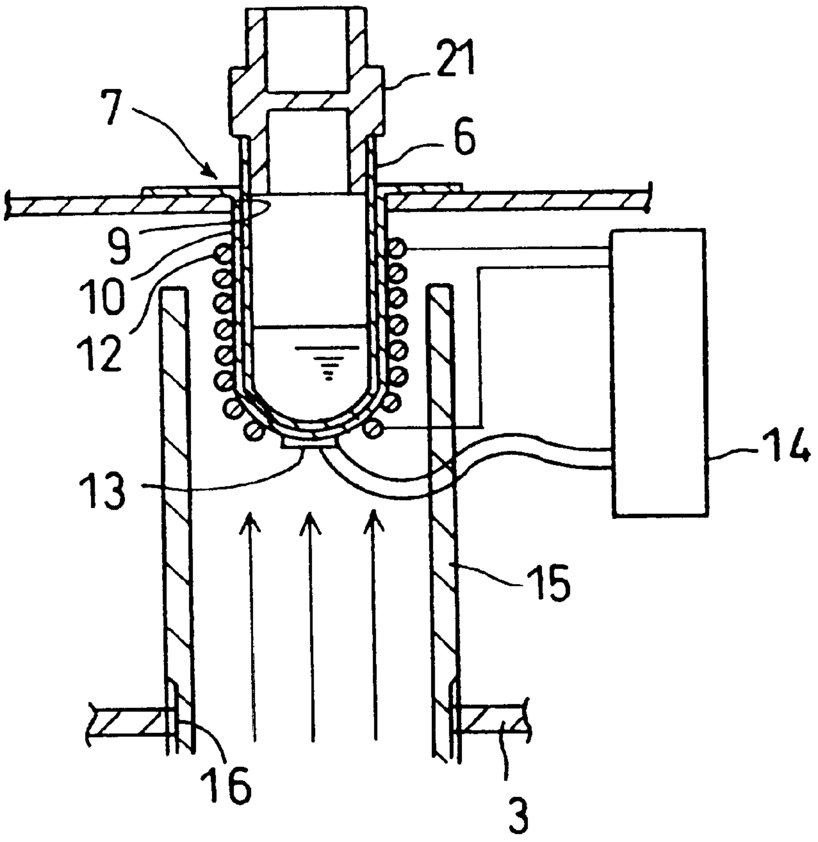
FIG. 10 is a longitudinal sectional view of a vicinity of a container of a fifth embodiment of a thermal cycler according to the invention.

FIG. 10 is a longitudinal sectional view of the containing member 10 and the nozzle 15 according to the fifth embodiment in which the nozzle 15 is formed in a shape of a hollow cylinder and is extended to cover the outer peripheral face of the containing member 10.

By constituting in this way, heat generated from the heater 12 can efficiently be used and air can be jetted to the containing member 10 without diffusing in the upper chamber (arrow marks in FIG. 10).

Sixth Embodiment

Next, an explanation will be given of a sixth embodiment of the invention in reference to FIG. 11.

The feature of the sixth embodiment resides in that the heater 12 is provided at inside of the nozzle 15.

Figure 11:
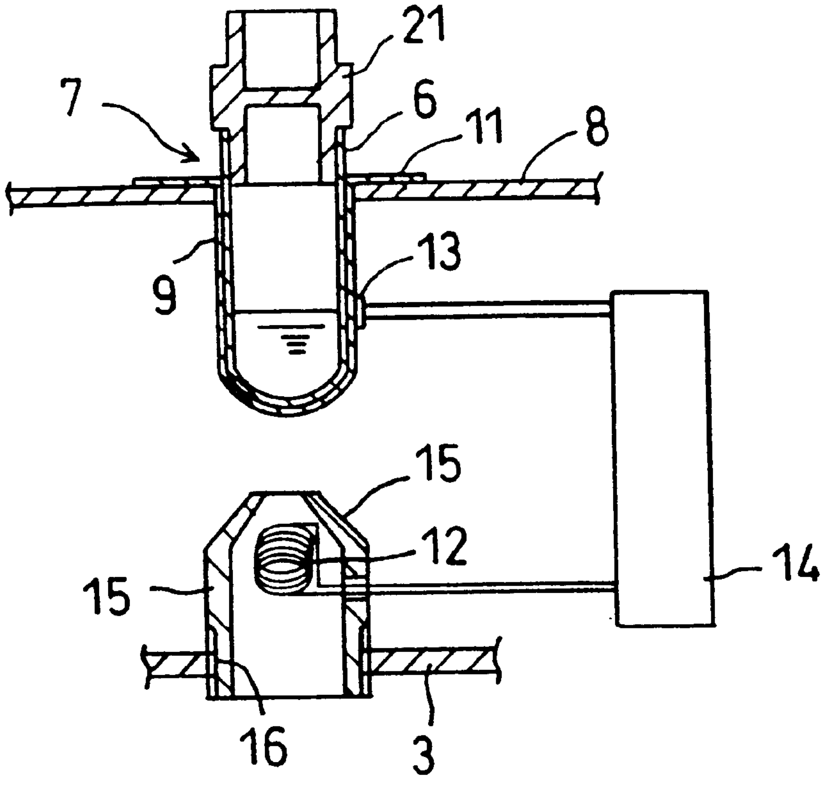
FIG. 11 is a longitudinal sectional view of a vicinity of a container of a sixth embodiment of a thermal cycler according to the invention.

FIG. 11 is a longitudinal sectional of the containing member 10 and the nozzle 15 according to the sixth embodiment in which the heater 12 is not present at the outer peripheral face of the containing member 10 and the heater 12 is provided at inside of the nozzle 15. The thermocouple 13 is provided at a side face of the outer peripheral face of the containing member 10.

According to such a constitution, the containing member 10 can be heated by heating air delivered from the blower 5 and jetting the heated air to the containing member 10.

Further, the control of the heater 12 is carried out by the control apparatus 14 based on the measurement result of the thermocouple 13.

According to the sixth embodiment described above, by heating the containing member 10 by jetting the heated air, temperature response of the containing member 10 can be promoted and temperature control can be facilitated.

Seventh Embodiment

Next, an explanation will be given of constitution of a seventh embodiment of the invention in reference to FIG. 12.

The feature of the seventh embodiment resides in that the micro tube 6 serves also as the containing member 10.

Figure 12:
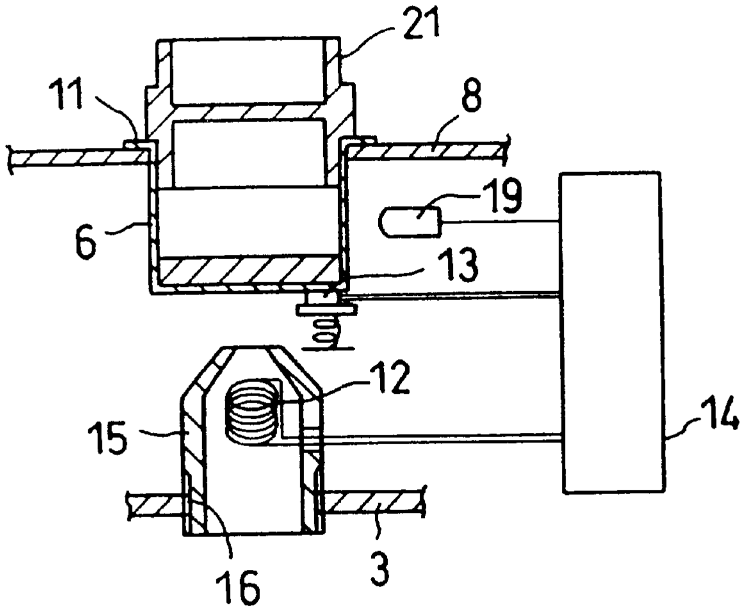
FIG. 12 is a longitudinal sectional view of a vicinity of a container of a seventh embodiment of a thermal cycler according to the invention.

FIG. 12 is a longitudinal sectional view of the micro tube 6 and the nozzle 15 according to the seventh embodiment in which air heated by the heater 12 in the nozzle 15 is jetted to the outer peripheral face of the micro tube 6 having a flat bottom and the micro tube 6 is directly heated. In fixing the micro tube 6 to the ceiling 8, the flange 11 which is also a portion of the micro tube 6 and the ceiling 8 are brought into contact with each other and fixed together. That is, when the micro tube 6 is not inserted, the upper chamber 3 can be observed from the through hole 9.

Further, the infrared temperature sensor 19 is arranged separately from the outer peripheral face of the micro tube 6 and the thermocouple 13 is arranged to be brought into contact with the flat bottom. The thermocouple 13 arranged to be brought into contact with the flat bottom is brought into contact therewith by being urged to the flat bottom by an elastic member such as spring. The infrared temperature sensor 19 and the thermocouple 13 measure temperature of the micro tube 6. The measured temperature is inputted to the control apparatus 14.

According to the seventh embodiment as described above, it is not necessary to confirm the state of contact between the containing member 10 and the micro tube 6 and accordingly, a time period for nucleic acid processing can be shortened and the temperature control can be carried out further easily.

Eighth Embodiment

Next, an explanation will be given of constitution of an eighth embodiment of the invention in reference to FIGS. 13(*a*) and 13(*b*).

The feature of the eighth embodiment resides in that a filter 24 is provided in the lower chamber 4.

Figure 13:
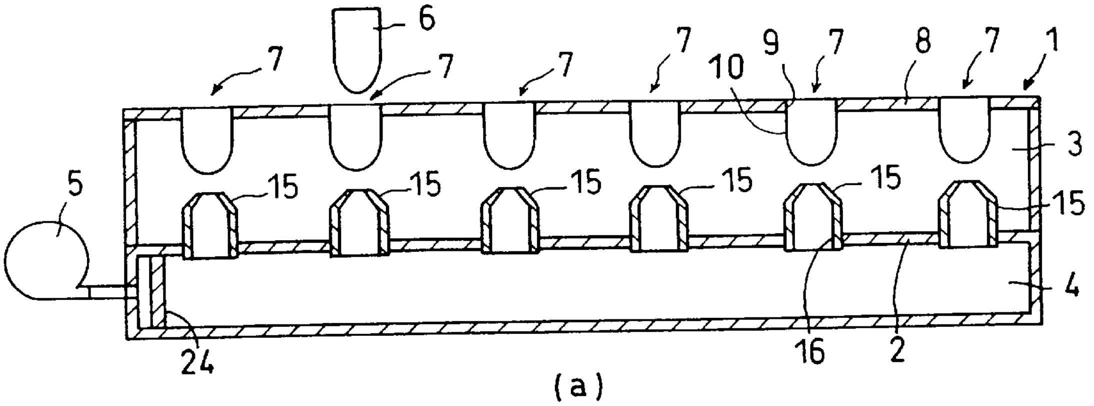
FIGS. 13(*a*) and 13(*b*) are longitudinal sectional views of a case of an eighth embodiment of a thermal cycler according to the invention.
Figure 13:
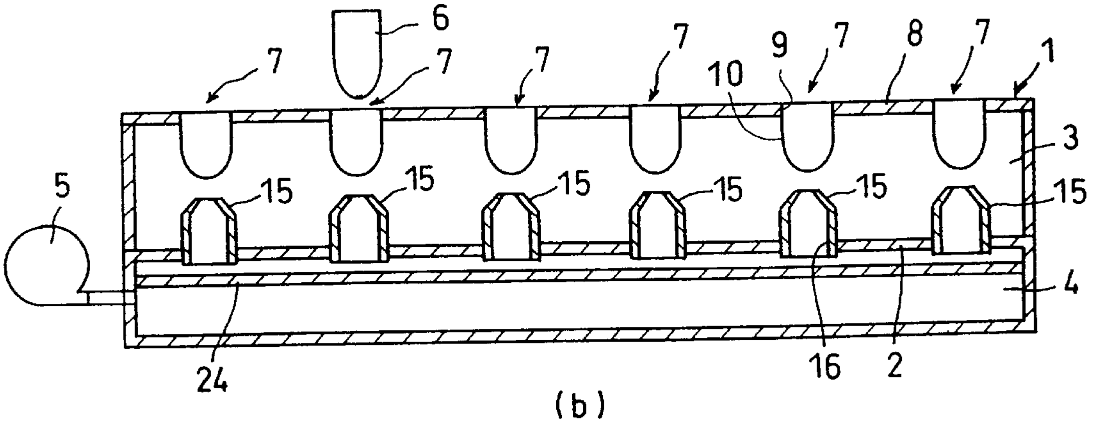

FIGS. 13(*a*) and 13(*b*) are longitudinal sectional views of the case 1 according to the eighth embodiment in which the filter 24 is provided substantially in the vertical direction at a vicinity of a portion in the lower chamber 4 where the blower 5 is connected (refer to FIG. 13(*a*)). Further, as shown by FIG. 13(*b*), the filter 24 is installed separately from the partition wall 2 to cover the respective through holes 16 substantially in parallel.

According to such a constitution, dust at outside of the thermal cycler 50 can be prevented from being introduced into the upper chamber 3. When foreign object such as dust or the like is assumedly adhered to the outer wall of the containing member 10, there is a concern of causing adverse influence on the containing member 10 and the thermocouple 13 by burning the dust, however, the adverse influence can be prevented.

Ninth Embodiment

Next, an explanation will be given of a ninth embodiment of the invention in reference to FIG. 14.

The feature of the ninth embodiment resides in that a plurality of fins 25 are provided at the outer peripheral face of the containing member 10.

Figure 14:
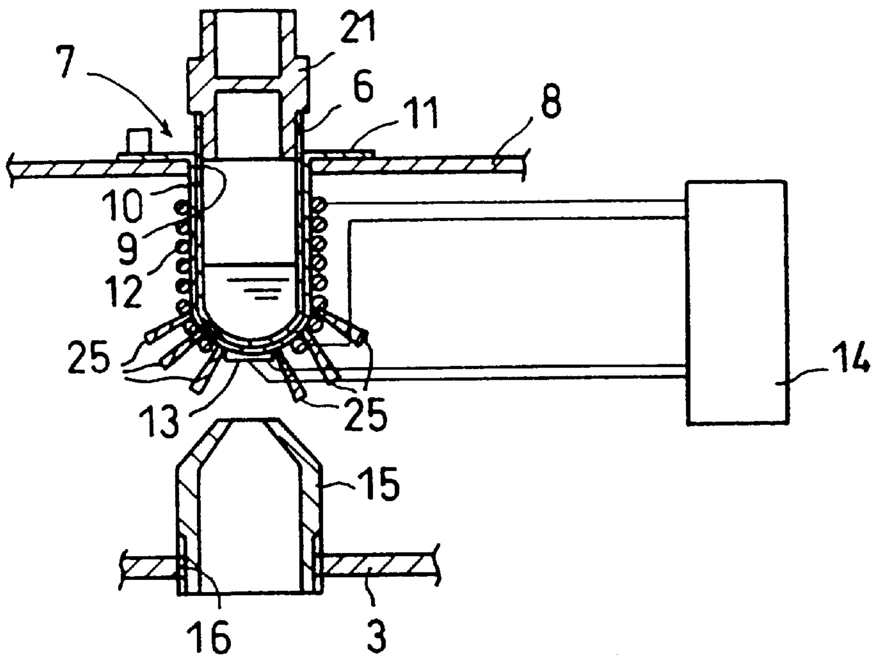
FIG. 14 is a longitudinal sectional view of a vicinity of a container of a ninth embodiment of a thermal cycler according to the invention.

FIG. 14 is a longitudinal sectional view of the containing member 10 and the nozzle 15 according to the ninth embodiment in which the plurality of fins 25 are provided at the outer peripheral portion of the containing member 10. The fin 25 is formed by a material having excellent heat conduction property. By installing the fins 25, the cooling effect can be promoted. Therefore, the time period required for nucleic acid processing can be shortened.

Tenth Embodiment

Figure 15:
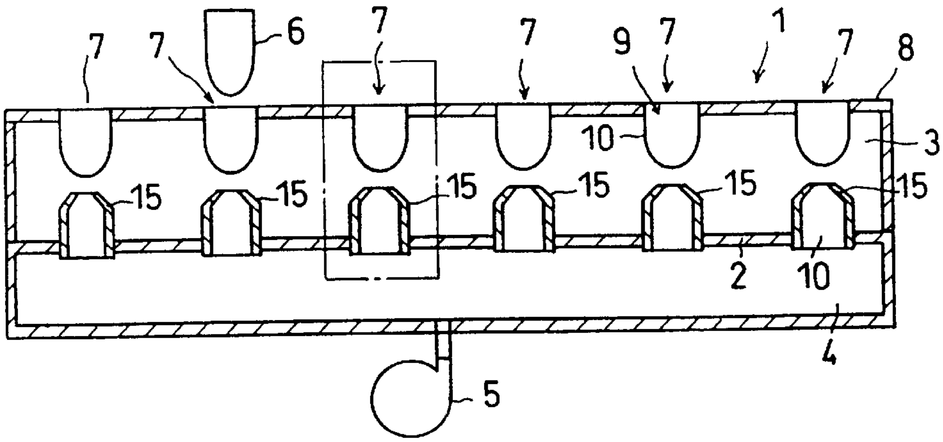
FIG. 15 is a longitudinal sectional case of a tenth embodiment of a thermal cycler according to the invention.

Next, an explanation will be given of a tenth embodiment of the invention in reference to FIG. 15.

The feature of the tenth embodiment resides in that the blower 5 is provided substantially at a central portion of the lower chamber 4.

The blower 5 is provided substantially at the central portion of the lower chamber 4. Preferably, the through holes 16 may be arranged to perforate substantially at symmetrical positions with the blower 5 at the center. Air is introduced from the substantial center of the lower chamber 4 to the respective through holes 16.

By such a constitution, temperature control can easily be carried out since substantially same amounts of air can be supplied to the respective holes 16 perforated at positions symmetrical with each other relative to the blower 5. Further, in the case in which the case 1 is formed in a cylindrical shape, when a contact portion of the case 1 and the blower 5 is arranged on a central axis of the case 1, substantially same amounts of air can be supplied to the respective through holes and heating or cooling efficiency can be promoted.

Eleventh Embodiment

Next, an explanation will be given of an eleventh embodiment of the invention in reference to FIGS. 16(*a*) and 16(*b*).

The feature of the eleventh embodiment resides in that the containing member 10 is formed by a shape memory alloy.

Figure 16:
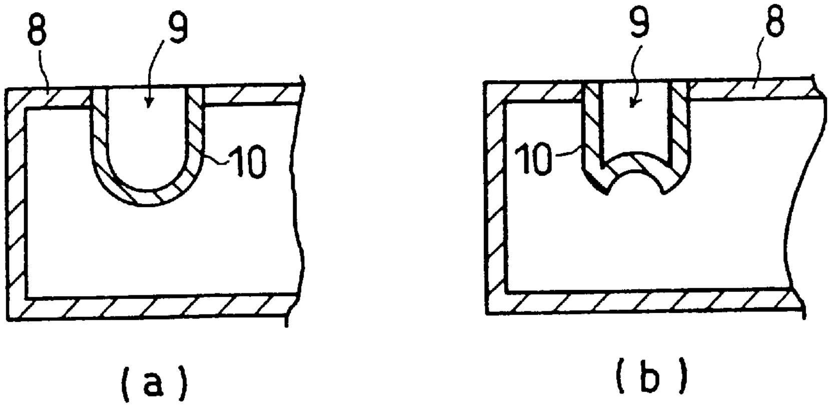
FIGS. 16(*a*) and 16(*b*) are sectional views of a container of an eleventh embodiment of a thermal cycler according to the invention.

FIGS. 16(*a*) and 16(*b*) are longitudinal sectional views of the containing member 10 according to the eleventh embodiment, showing the containing member 10 having a shape of the micro tube 6 as shown by FIG. 16(*a*) when temperature of the micro tube 6 is substantially temperature equal to or lower than 95° C. and memorizing a state in which a vicinity of a bottom portion of the containing member 10 is formed in a shape protruded upwardly as shown by FIG. 16(*b*) when the temperature of the micro tube 6 is equal to or higher than 95° C. and equal to or lower than 100° C. By deforming the containing member 10 as shown by FIG. 16(*b*), heat amount transferred from the heater 12 to the micro tube 6 can be reduced.

According to the eleventh embodiment, DNA having the double helix structure can be prevented from being destructed at 100° C. or higher.

Twelfth Embodiment

Next, an explanation will be given of constitution of a twelfth embodiment of the present invention in reference to FIG. 17.

The feature of the eleventh embodiment resides in that lamps 26*a* and 26*b* showing the processing state of the micro tube 6 to the user are provided.

Figure 17:
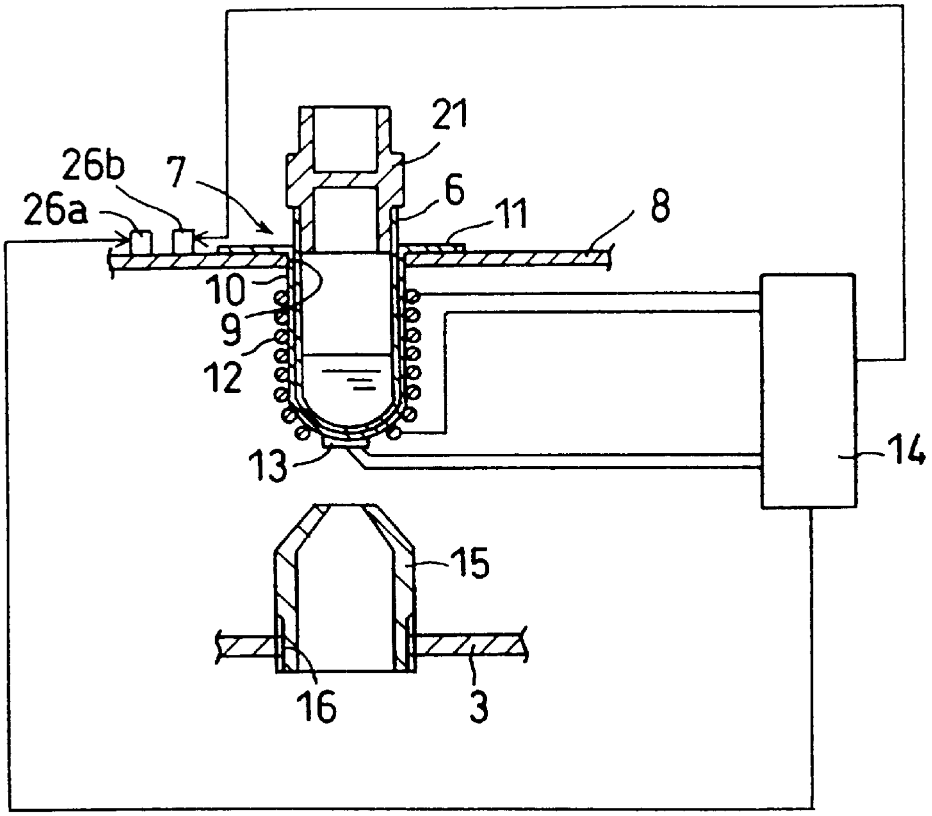
FIG. 17 is a longitudinal sectional view of a vicinity of a container of a twelfth embodiment of a thermal cycler according to the invention.

FIG. 17 is a longitudinal sectional view of the containing member 10 and the nozzle 15 according to the twelfth embodiment in which the blue lamp 26*a* and the red lamp 26*b* are provided at a vicinity of the respective micro tube 6 at surface of the ceiling 8. The respective lamps are connected to the control apparatus 14 and operate to switch on and switch off in accordance with a control signal of the control apparatus 14. For example, when the temperature of the micro tube 6 is equal to or lower than room temperature, only the blue lamp 26*a* is controlled to switch on and when the temperature is equal to or higher than room temperature, only the red lamp 26*b* is controlled to switch on. Therefore, the user can take out the micro tube 6 which has been processed by confirming that the blue lamp 26*a* is switched on and can insert a new one of the micro tube 6 which has not been processed.

Further, the method of showing the processing state of the respective micro tube 6 to the user can also be carried out by displaying information on a display such as a liquid crystal panel 53 provided on the case 1.

According to the twelfth embodiment, by showing the processing state of the respective micro tube 6 to the user, further swift processing can be carried out.

Thirteenth Embodiment

Next, an explanation will be given of constitution of a thirteenth embodiment of the invention in reference to FIG. 18.

The feature of the thirteenth embodiment resides in that an exhaust portion 27 connected to a duct 26 for exhausting air is provided at the lower chamber 4 opposed to the introducing portion for introducing air from the blower 5.

Figure 18:
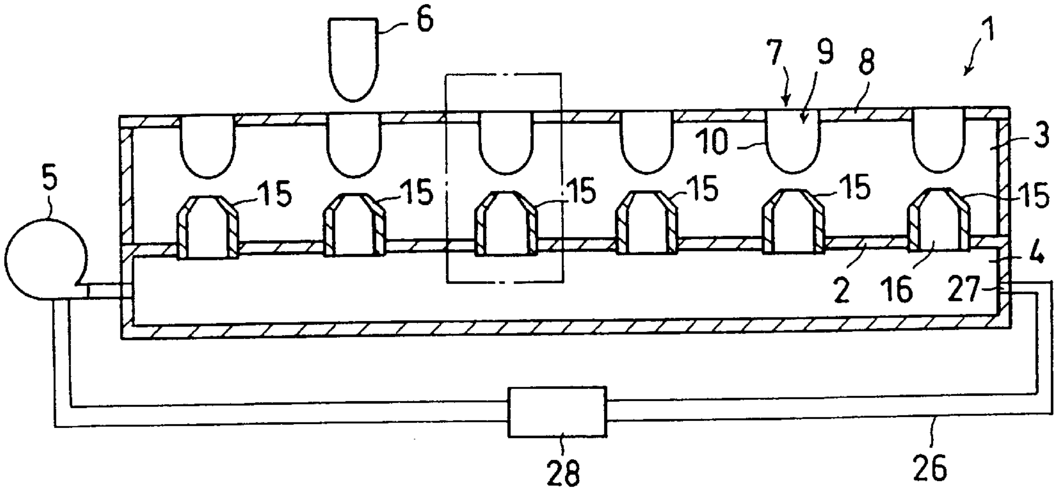
FIG. 18 is a longitudinal sectional view of a case of a thirteenth embodiment of a thermal cycler according to the invention.

FIG. 18 is a longitudinal sectional view of the case 1 according to the thirteenth embodiment in which the exhaust portion 27 is provided at a portion opposed to the introducing portion for introducing air from the blower 5 to the lower chamber 4. The exhaust portion 27 is connected to the duct 26 and air flows in the duct 26. The duct 26 is connected to the blower 5 and returns air which has been exhausted once from the lower chamber 4. Further, a heat exchanger 28 is provided at a middle of the duct 26 and the heat exchanger 28 takes heat from air which has passed through the exhaust portion 27. That is, temperature of air flowing before and after the heat exchanger 28 differs and temperature of air at an inlet of the heat exchanger 28 is higher than temperature at an outlet thereof.

Further, the exhaust portion 27 may be provided at the upper chamber 3. When the exhaust portion 27 is provided at the lower chamber 4, an amount of exhausted air is to the degree of not losing function of air flowed from the nozzle 15, that is, function of heating or cooling.

Fourteenth Embodiment

Next, an explanation will be given of constitution of a fourteenth embodiment of the invention in reference to FIGS. 19(*a*) and 19(*b*).

The feature of the fourteenth embodiment resides in that protruded portions are provided at portions of opening portions of the micro tube 6 and the containing member 10.

Figure 19:
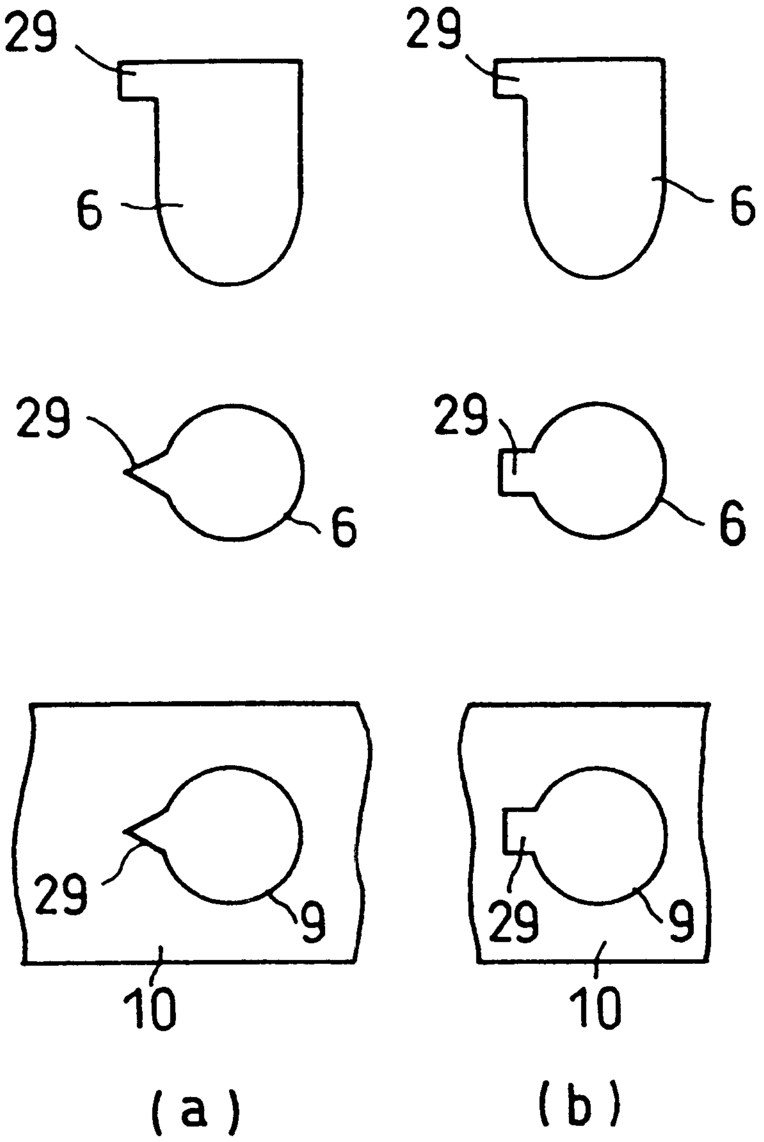
FIGS. 19(*a*) and 19(*b*) are side views and top views of micro tubes and top views of containing members of a fourteenth embodiment of a thermal cycler according to the invention.

FIGS. 19(*a*) and 19(*b*) illustrate side views and top views of micro tubes and top views of containing members according to the fourteenth embodiment in which upper stages of FIGS. 19(*a*) and 19(*b*) are side views of the micro tubes 6, middle stage thereof are top views of the micro tubes 6 and lower stage thereof are top views of the containing members 10. In FIG. 19(*a*), a projected portion 29 is formed at the opening portion of the micro tube 6. The through hole 9 of the containing member 10 is perforated with a projected portion 30 to coincide with the projected portion 29 of the micro tube 6. The projected portion 29 of the micro tube 6 is inserted to fit to the projected portion 30 of the through hole 9.

When the projected portion 29 and the projected portion 30 are not fitted to each other, the indicator 17 provided at the micro tube 6 cannot be read by the optical sensor 18 and is dealt with as insertion failure. Further, the shape of the projected portion may be a shape as shown by FIG. 19(*b*). Further, the indicator 17 is provided at a position which can be read by the optical sensor 18 in a state in which the projected portion 29 and 30 are fitted with each other.

According to such a constitution, the insertion failure of the micro tube 6 and the containing member 10 can be reduced.

Fifteenth Embodiment

Next, an explanation will be given of a fifteenth embodiment of the invention.

The feature of the fifteenth embodiment resides in that the ceiling 8 is attachable and detachable.

The ceiling 8 is mechanically connected to the case 1 by magnetic force, screw or the like and is attachable and detachable as necessary. There are a plurality of kinds of the attachable and detachable ceilings 8 and the through holes 9 having various sizes are prepared to the respective ceilings 8. Therefore, the ceiling 8 can be switched pertinently according to the size of the micro tube 6. However, according to the positional relationship between the through hole 9 and the nozzle 15, the through hole 9 and the nozzle 15 are arranged such that a central axis of the through hole 9 and a central axis of the nozzle 15 substantially coincide with each other.

According to such a constitution, even the micro tubes 6 having different diameters can be processed by interchanging the ceilings 8.

Sixteenth Embodiment

Next, an explanation will be given of constitution of a sixteenth embodiment of the invention in reference to FIG. 20.

The feature of the sixteenth embodiment resides in that a cooling pipe 31 is wound on the outer peripheral face of the containing member 10.

Figure 20:
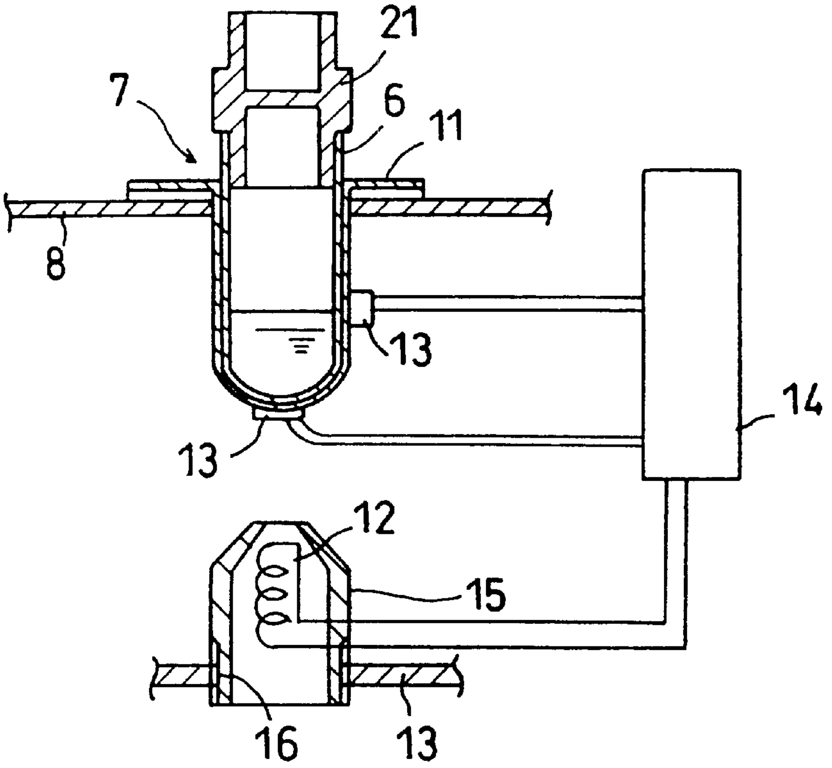
FIG. 20 is a longitudinal sectional view of a vicinity of a container of a sixteenth embodiment of a thermal cycler according to the invention.

FIG. 20 is a longitudinal sectional view of the containing member 10 and the nozzle 15 according to the sixteenth embodiment in which the cooling pipe 31 is wound around the outer peripheral face of the containing member 10. Further, the cooling pipe 31 is formed by a material having excellent heat conductivity (copper, aluminum or the like).

The micro tube 6 in the containing member 10 is cooled by flowing a cooling medium, for example, water in the cooling pipe 31. The cooling pipe 31 may be replaced by a Pertier element, a heat pipe or a heat pump so far as it is coolable.

According to such a constitution, cooling time can be shortened by cooling by jetting air from the nozzle 15 and cooling by the cooling pipe 31.

Further, the present invention is not limited to the above-described respective embodiment but can naturally be carried out by variously modifying the present invention within the range not deviated from the gist. For example, the medium may not be air but may be a liquid, for example, water.

Further, as the method of heating the containing member, a heat pipe may be wound around the containing member in place of an electric wire and the containing member may be heated by using the heat pipe. Further, heating can also be carried out by providing a Pertier element or a heat pump at the containing member. Further, the respective containing member may be heated by heat radiation by providing a radiation object at a vicinity of the respective containing member. Further, the respective containing member may be heated by induction heating of radio wave (for example, microwave) by arranging a heating coil around the respective containing member. Further, a light source may be provided at a vicinity of the containing member.

Further, temperature of the sample can also be measured by mixing a liquid crystal thermometry enclosed in a microcapsule in sample in place of the infrared temperature sensor and detecting reflected light from the liquid crystal in the microcapsule by an optical sensor. The liquid crystal thermometry is a substance in which orientation of crystal is changed by temperature around the liquid crystal. Further, temperature of the sample may be measured by mixing a fluorescent member having different color of emitting light by temperature in the sample and measuring reflected light of the fluorescent member.

Further, although a single piece of the micro tube is inserted into a single one of the well, when the size of the well can allow to insert a plurality of micro tubes, a lubricant of grease, water or the like may be injected into the well and the plurality of micro tubes may be dipped to the lubricant to thereby carry out the processing.

As has been explained, according to the present invention, highly accurate temperature control can independently be carried out with regard to the individual micro tube.

What is claimed is:

1. A thermal cycler comprising:

a plurality of wells capable of containing micro tubes holding a sample including nucleic acid;

a plurality of heaters provided at the respective wells directly or indirectly heating the micro tubes;

a plurality of temperature sensors, each measuring temperature of the respective micro tubes;

a control apparatus inputted with measured values of the temperature sensors, supplying current to the plurality of heaters based on the measured values and controlling the temperature of the respective micro tubes independently from each other; and a plurality of nozzles provided at the respective wells jetting a medium to the wells or the micro tubes in order to cool down the micro tubes; and wherein the control apparatus controls the temperature of the micro tubes by jetting the medium from the nozzles to the wells when the current is supplied to the heaters.

2. The thermal cycler according to claim 1:

wherein the temperature sensors are provided in contact with outer walls of the wells or in noncontact with the micro tubes or the wells at positions capable of measuring the temperature of the sample.

3. The thermal cycler according to claim 1, further comprising:

a plurality of luminance sensors measuring a luminance of the respective sample the wells.

4. The thermal cycler according to claim 1:

wherein the nozzles are separated from the wells and provided to cover outer peripheral faces of the wells.

5. A thermal cycler comprising:

a plurality of wells capable of containing micro tubes holding a sample including nucleic acid and pasted with an indicator which differs in accordance with the respective sample;

a plurality of pick up sensors detecting the respective indicator;

a plurality of heaters provided at the respective wells directly or indirectly heating the micro tubes;

a control apparatus inputted with measured values of the temperature sensors, supplying a current to the respective heaters based on the measured values and controlling the temperature of the respective micro tubes independently from each other by a previously stored temperature pattern in correspondence with the indicator.

6. A DNA amplifier method having a control apparatus controlling to heat a plurality of micro tubes holding a sample including nucleic acid independently from each other by a plurality of heat apparatus provided at the respective micro tubes based on measured values of a plurality of temperature sensors provided at the respective micro tubes and storing a temperature pattern heating the micro tubes, said DNA amplifier method comprising:

a step of reading the temperature pattern set for the respective micro tubes by the control apparatus;

a step of generating a signal for operating the respective heat apparatus based on the measured values and the temperature pattern by the control apparatus;

a step of inputting the generated signal to the respective heat apparatus, heating the respective micro tubes independently from each other based on the signal by the heat apparatus and having a desired reaction carry out in the micro tubes; and a step of outputting a signal stopping operation of the heat apparatus to the respective heat apparatus based on the temperature pattern by the control apparatus.

7. The DNA amplifier method according to claim 6, wherein in heating the micro tubes, a medium is jetted from nozzles provided proximately to the respective micro tubes and capable of jetting the medium at the respective micro tubes.

8. A DNA amplifier method having a control apparatus controlling to heat a plurality of micro tubes holding a sample including nucleic acid and pasted with an indicator which differs in accordance with the respective sample independently from each other by a plurality of heat apparatus provided at the respective micro tubes based on measured values of a plurality of temperature sensors provided at the respective micro tubes and storing a temperature pattern heating the micro tubes, said DNA amplifier method comprising:

a step of detecting the indicator and setting the temperature pattern in correspondence with the detected indicator by the control apparatus;

a step of generating a signal operating the respective heat apparatus based on the measured values and the temperature pattern by the control apparatus;

a step of inputting the generated signal to the respective heat apparatus, heating the respective micro tubes independently from each other based on the signal by the heat apparatus and having a desired reaction carry out in the micro tubes; and a step of outputting a signal stopping operation of the heat apparatus to the respective heat apparatus based on the temperature pattern by the control apparatus.

9. The DNA amplifier method according to claim 8:

wherein the heat apparatus are controlled by the control apparatus such that the micro tubes are heated to about 60° C. and held for a constant time period, thereafter, the micro tubes are heated to about 95° C. and held for a constant time period.

10. The DNA amplifier method according to claim 9, further comprising:

a step of measuring a luminance of the sample in the micro tubes after holding the micro tubes at temperature of about 60° C. for the constant time.

* * * * *